United States Patent
Katra et al.

(10) Patent No.: US 10,912,514 B2
(45) Date of Patent: *Feb. 9, 2021

(54) APPARATUS AND METHOD FOR DETECTION OF SLEEP DISORDERED BREATHING

(71) Applicant: Greatbatch Ltd., Clarence, NY (US)

(72) Inventors: Rodolphe Katra, Blaine, MN (US); Niranjan Chakravarthy, Eden Prairie, MN (US)

(73) Assignee: Greatbatch Ltd., Clarence, NY (US)

( * ) Notice: Subject to any disclaimer, the term of this patent is extended or adjusted under 35 U.S.C. 154(b) by 151 days.

This patent is subject to a terminal disclaimer.

(21) Appl. No.: 16/170,542

(22) Filed: Oct. 25, 2018

(65) Prior Publication Data

US 2019/0059816 A1 Feb. 28, 2019

Related U.S. Application Data

(62) Division of application No. 14/208,021, filed on Mar. 13, 2014, now Pat. No. 10,130,306.

(60) Provisional application No. 61/785,495, filed on Mar. 14, 2013.

(51) Int. Cl.
  *A61B 5/00* (2006.01)
  *A61B 5/0205* (2006.01)
  *A61B 5/08* (2006.01)

(52) U.S. Cl.
  CPC .......... *A61B 5/6847* (2013.01); *A61B 5/0205* (2013.01); *A61B 5/0803* (2013.01); *A61B 5/4818* (2013.01); *A61B 5/0031* (2013.01)

(58) Field of Classification Search
  CPC ... A61B 5/6847; A61B 5/4818; A61B 5/0803; A61B 5/003
  See application file for complete search history.

(56) References Cited

U.S. PATENT DOCUMENTS

| 5,924,979 | A | 7/1999 | Swedlow et al. |
| 7,073,501 | B2 | 7/2006 | Remmers et al. |
| 7,160,252 | B2 * | 1/2007 | Cho ............ A61B 5/0205 600/323 |

(Continued)

FOREIGN PATENT DOCUMENTS

| EP | 2008581 | 12/2008 |
| WO | 2004112606 A1 | 12/2004 |

OTHER PUBLICATIONS

European Search Report from EP App. No. 14159795.5 dated Jun. 11, 2014, 8 pages.

*Primary Examiner* — Rex R Holmes
*Assistant Examiner* — Sana Sahand
(74) *Attorney, Agent, or Firm* — Michael F. Scalise

(57) ABSTRACT

An apparatus, system, and method directed to detecting a physiological signal during discrete time separated detection windows, deriving one or more respiratory disturbance indices from the physiological signal, detecting a respiratory disturbance state in response to the one or more respiratory disturbance indices deviating from a threshold value, interpolating the one or more respiratory disturbance indices between adjacent time separated detection windows, and declaring a respiratory disturbance episode based on the detected respiratory disturbance state during the detection windows and the interpolation between detection windows.

22 Claims, 14 Drawing Sheets

(56) References Cited

U.S. PATENT DOCUMENTS

| | | | |
|---|---|---|---|
| 7,179,229 B1 * | 2/2007 | Koh | A61B 5/0215 |
| | | | 600/483 |
| 8,023,928 B2 * | 9/2011 | Fulks, III | G01R 19/2506 |
| | | | 324/378 |
| 8,180,442 B2 | 5/2012 | Belalcazar et al. | |
| 8,280,499 B2 | 10/2012 | Brockway et al. | |
| 8,321,022 B2 | 11/2012 | Stahmann et al. | |
| 8,688,219 B2 * | 4/2014 | Ransom | A61B 5/036 |
| | | | 600/529 |
| 10,130,306 B2 * | 11/2018 | Katra | A61B 5/0803 |
| 2006/0041201 A1 | 2/2006 | Behbehani et al. | |
| 2007/0032733 A1 | 2/2007 | Burton | |
| 2007/0167843 A1 | 7/2007 | Cho et al. | |
| 2008/0161713 A1 | 7/2008 | Leyde et al. | |
| 2009/0156908 A1 | 6/2009 | Belalcazar et al. | |
| 2014/0275837 A1 | 9/2014 | Katra et al. | |

* cited by examiner

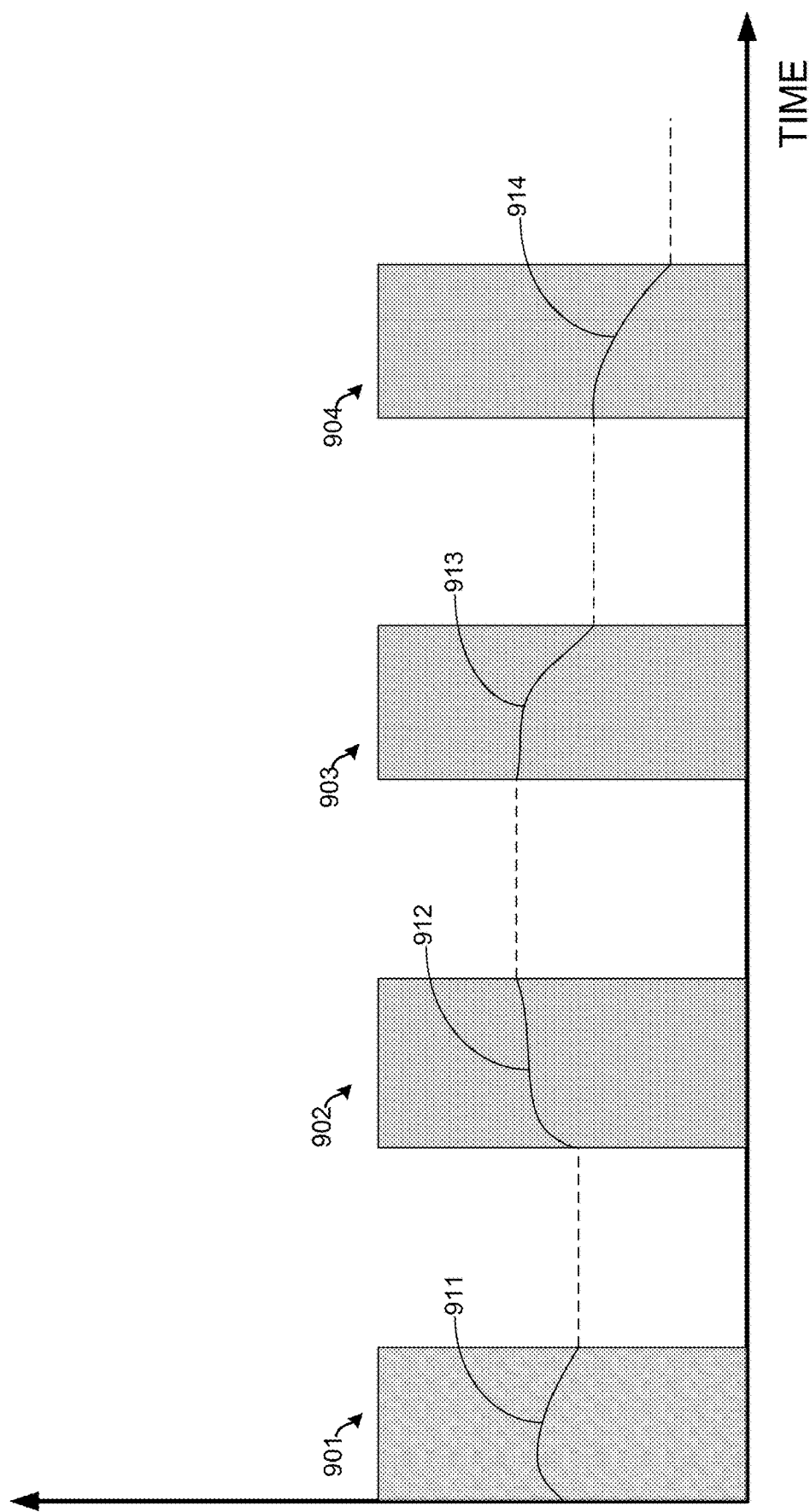

APPARATUS AND METHOD FOR DETECTION OF SLEEP DISORDERED BREATHING

RELATED APPLICATIONS

This application is a divisional of U.S. patent application Ser. No. 14/208,021, filed Mar. 13, 2014, which claims the benefit of Provisional Patent Application Ser. No. 61/785,495, filed on Mar. 14, 2013, and which are incorporated herein by reference in their entireties.

TECHNICAL FIELD

This patent document pertains generally to patient health monitoring, and more particularly, to monitoring respiratory activity for indications of disordered breathing.

BACKGROUND

The human body functions through a number of interdependent physiological systems controlled through various mechanical, electrical, and chemical processes. Electrical signals cause a heart to beat. In a healthy patient, regular heart beats pump blood through the cardiovascular system. The human cardiovascular system is responsible for receiving oxygen-deprived blood into the heart from the venous system of the body, delivering the oxygen-deprived blood to the lungs to be replenished with oxygen, receiving the oxygenated blood from the lungs back into the heart, and delivering the oxygenated blood to the body via the arterial vasculature. The respiratory system, through the breathing mechanism, performs the function of exchanging oxygen and carbon dioxide with the external environment.

Various disorders may affect the cardiovascular, respiratory, and other physiological systems. Breathing disorders include various forms of rhythm-related disorders such as sleep apnea and hypopnea. Disordered breathing is a respiratory system condition that affects a significant number of the population, particularly between the ages of 30 and 60 years.

Various types of disordered respiration have been identified, including, apnea (interrupted breathing), hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Cheyne-Stokes respiration is particularly prevalent among heart failure patients, and may contribute to the progression of heart failure.

Sleep disordered breathing is particularly prevalent and is associated with excessive daytime sleepiness, systemic hypertension, increased risk of stroke, angina and myocardial infarction. Disordered breathing can be particularly serious for patients concurrently suffering from cardiovascular deficiencies.

Various aspects of cardiac activity (e.g., heart rate, arrhythmias) can be detected by measuring, recording, and analyzing cardiac electrical signals, such as an electrocardiogram (ECG) signal. One way of measuring ECG signals involves attaching electrodes, typically ten, externally to a patient's skin and sensing the electrical signals that form the ECG waveform.

Implantable monitoring systems can be implanted under the skin with electrodes that sense subcutaneous electrical signals, including ECG signals, which are analyzed as being indicative of cardiac activity. In such systems, the electrodes also receive extraneous non-cardiac electrical signal information, which is typically filtered out to produce a more readable ECG. Non-cardiac electrical signals can be generated by muscle tissues during physical activity, for example. In some examples, an implantable loop recorder (ILR) can record and quantify patient heart electrical activity.

SUMMARY

Various techniques and related methods, apparatuses and systems are described. In one embodiment, a method includes detecting a physiological signal during discrete time separated detection windows, deriving one or more respiratory disturbance indices from the physiological signal, detecting a respiratory disturbance state in response to the one or more respiratory disturbance indices deviating from a threshold value, interpolating the one or more respiratory disturbance indices between adjacent time separated detection windows, and declaring a respiratory disturbance episode based on the detected respiratory disturbance state during the detection windows and the interpolation between detection windows.

In another embodiment, a system is described that includes a waveform acquisition apparatus and analyzer. The waveform acquisition apparatus is operable to detect a physiological signal during discrete time separated detection windows. The waveform acquisition apparatus is non-operable for detecting the physiological signal during a time between the discrete time separated detection windows. The analyzer includes first processing circuitry, second processing circuitry, and third processing circuitry. The first processing circuitry derives one or more respiratory disturbance indices from the physiological signal and detects if the one or more respiratory disturbance indices deviate from a threshold value. The second processing circuitry interpolates the one or more respiratory disturbance indices between adjacent time separated detection windows. The third processing circuitry declares a respiratory disturbance episode based on the detected respiratory disturbance state during the detection windows and the interpolation between detection windows.

In another aspect, an apparatus includes electrodes, a data acquisition module, and an analyzer. The electrodes are adapted to acquire ECG waveforms from an implanted subcutaneous extrathoracic location of a patient. The data acquisition module captures the ECG waveforms during discrete time separated detection windows. The data acquisition module is non-operable for detecting the ECG waveforms during a time between the discrete time separated detection windows. The analyzer module includes first processing circuitry, second processing circuitry, and third processing circuitry. The first processing circuitry derives one or more respiratory disturbance indices from the physiological signal and detects if the one or more respiratory disturbance indices deviate from a threshold value. The second processing circuitry interpolates the one or more respiratory disturbance indices between adjacent time separated detection windows. The third processing circuitry declares a respiratory disturbance episode based on the detected respiratory disturbance state during the detection windows and the interpolation between detection windows.

The above summary is not intended to describe each disclosed embodiment or every implementation of the present disclosure. The figures and the detailed description below more particularly exemplify illustrative embodiments

BRIEF DESCRIPTION OF THE DRAWINGS

Throughout the specification reference is made to the appended drawings, where like reference numerals designate like elements, and wherein:

FIG. 9 is a graph showing a changing disordered breathing state such as an apnea state according to one embodiment;

Figure 1:
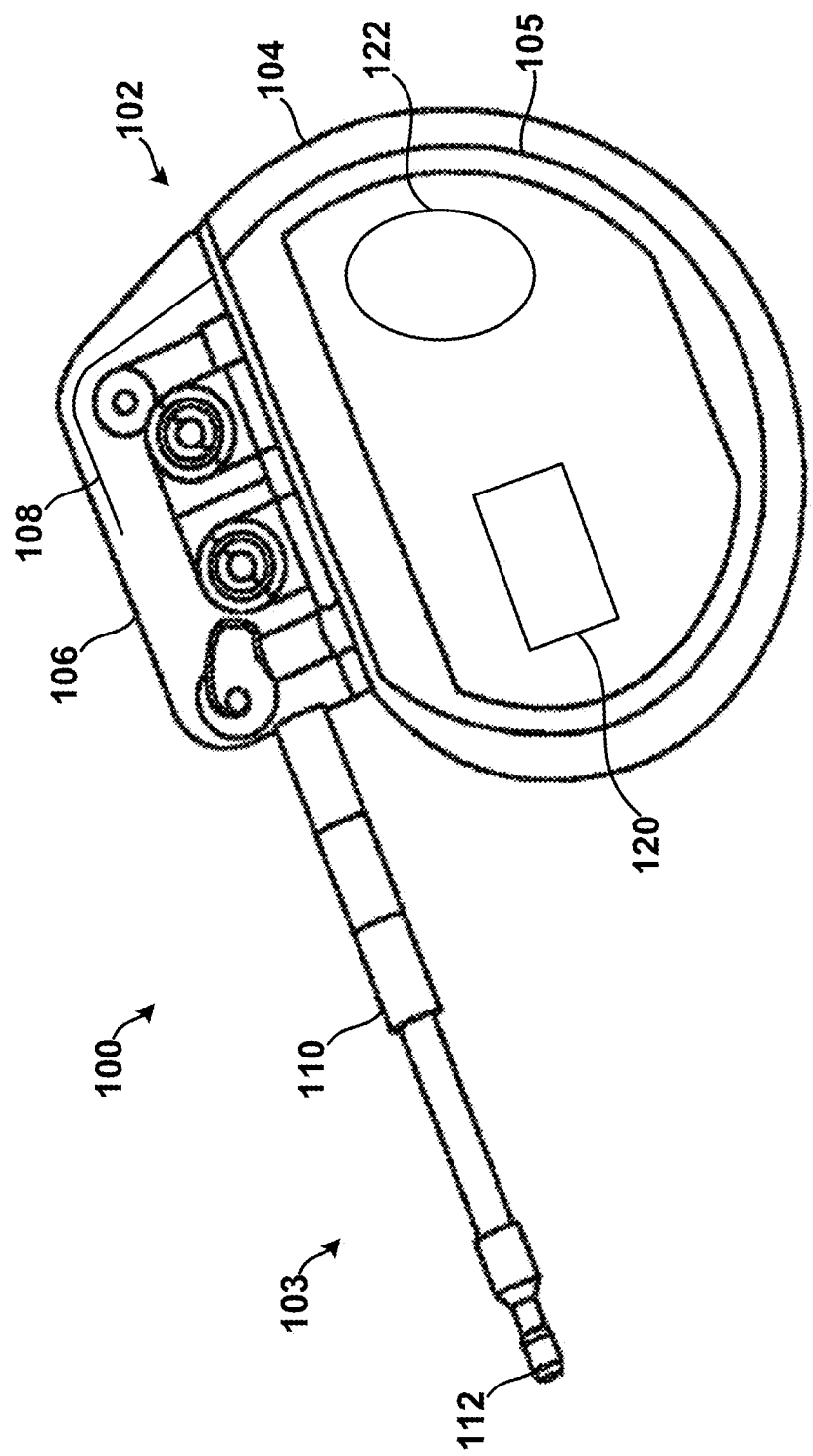
FIG. 1 is a perspective of a representative implantable device that can be subcutaneously implanted under a patient's skin.

The figures are not necessarily to scale. Like numbers used in the figures refer to like components. However, it will be understood that the use of a number to refer to a component in a given figure is not intended to limit the component in another figure labeled with the same number. The drawings illustrate generally, by way of example, but not by way of limitation, various examples discussed in the present document.

DETAILED DESCRIPTION

The present disclosure describes techniques and related methods, devices, and systems for monitoring patient breathing for indications of disordered breathing. Additionally, the present disclosure describes techniques and related methods, devices, and systems for remote monitoring and data collection, as well as data presentation and organization. In some instances, the described monitoring techniques can be used to trigger the application of therapy for the disordered breathing condition. In further embodiments, the present inventors have recognized, among other things, that sleep apnea is a co-morbidity for several cardiac conditions. The present inventors have further recognized that it is desirable to provide a device or method for monitoring and/or detecting sleep apnea in cardiac patients.

In the following detailed description, reference is made to the accompanying drawings which form a part hereof, and in which is shown by way of illustration specific examples in which the present description may be practiced. These examples are described in sufficient detail to enable those skilled in the art to practice the present subject matter, and it is to be understood that other examples may be utilized and that structural changes may be made without departing from the scope of the present description. Therefore, the following detailed description is not to be taken in a limiting sense.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, or process that includes elements in addition to those listed after such a term are still deemed to fall within the scope of the description. Moreover, the terms "first," "second," and "third," etc. are used merely as labels, and are not intended to impose numerical requirements on their objects.

Implantable devices that monitor cardiac physiologic activity are frequently implanted subcutaneously under a patient's skin of the chest. An implantable loop recorder (ILR) is an example of such a device that may be implanted in this fashion. The following description can be used, in some examples, with the ILR as part of a monitoring system. However, the invention refers to a method of detecting and/or monitoring disordered breathing including apnea that is independent of the platform it is incorporated in. For example, the invention could be implemented in an external sensing device, like a Holter monitor or an active therapeutic implantable system, like a pacemaker, a defibrillator, or the like. In various examples, the following description pertains to a complete ILR system as well as an ILR system's sub-components (e.g., ASIC). The ILR device may be leadless or may include one or more subcutaneous leads.

Other physiologic parameters or combinations of parameters, such as other electrical physiologic signals (e.g., EMG signal, bio-impedance signal), mechanical signals (e.g., blood pressure signal, blood flow signal, pulse oximetry), chemical signals (e.g., glucose), temperature and the like may similarly be recorded by the device in various implementations. In some examples, an ILR device measures ECG in real-time. While there is sleep apnea-related diagnostic information in ECG data (e.g., tidal volume), it may not be directly used by polysomnography specialists for sleep staging. In some examples, additional sensors, such as pulse oximeter, bioimpedance, activity, and temperature sensors, can be combined in two ways. In some examples, all sensors reside on the ILR and transmit information to the personal diagnostic monitor (PDM). In some examples, the sensors can be deployed separately and can each communicate with the PDM, which can combine and/or process the information sources for further processing or display.

In some examples, the ILR transmits three kinds of data strips: symptomatic, asymptomatic, and trending. In some examples, trending data strips are basically fixed duration recordings that happen at regular intervals, for instance, every 7.5 minutes, 15 minutes, 4 hours, etc., based on user setting. The individual strips can be analyzed, on the ILR or on the PDM or offline on servers, for apnea activity. There are several methods to do so. For instance, in some examples, if the objective is to detect sleep apnea with retrospective data, the trending data can be time ordered and analyzed in two ways. Starting with the first trending strip, an algorithm or manual reader can track the apnea status for the strip duration and retain the ending apnea state. For the next strip, the initial condition can be set to the end apnea state of the previous strip. With reference to FIG. 9, an example of the changing apnea state can be seen.

In some examples, a certain variation (can be measured as standard deviation, signal variance, personalized change, normalized index, or adaptive threshold, as examples) in an apnea index (defined as tidal volume intensity, periodicity, or turbulence, as examples) can be assessed in a variety of ways (such as per strip, per day, per hour, per nocturnal period, or the like, as examples), to yield a measure of apnea status in a patient. The apnea index can be derived from the non-cardiac component of the ECG electrical signal and used in isolation or in correlation with changes to cardiac activity, such as absolute heart rate, changes in heart rhythm, and/or changes in cardiac response to autonomic regulation, such as cardio-acceleration/cardio-deceleration, as an example.

In some examples, an ILR system can be configured to detect apnea for each trending strip and detect apnea onset if a certain proportion of strips are detected to correspond to apnea. The apnea detection can be done immediately after reception or after sufficient data has been collected.

In some examples, the apnea state can also be detected on the trending-data in real-time in order to actively track patient apnea state in order to provide closed-loop therapy via Continuous Positive Airway Pressure (CPAP).

In some examples, an ILR system can have the apnea detection on the ILR and perform a signal capture upon apnea detection (e.g., an apnea AHI (Apnea-Hypopnea Index) score can be used as the threshold). In various examples, all sensor signals can be captured, or only the ones where apnea was detected.

In some examples, the ILR can transmit data in real-time to the closed-loop therapy device. If battery consumption is an issue, in some examples, the ILR can use a low-power transmission to the PDM, and the PDM can transmit apnea information to the therapy system.

In some examples, the ILR can monitor in the normal clinician-set mode at all times. However, in further examples, an additional mode can be added to analyze/transmit signals when the patient presses a sleep button on the PDM. In some examples, this can enable battery-intensive data transmission only during sleep instances.

In various examples, the ILR/PDM can either transmit an apnea present/absent signal or an index similar to the AHI. In some examples, using the first scheme, the closed-loop therapy can resemble a bang-bang controller. In some examples, using the second scheme, the closed-loop therapy can be made via a proportional-integral type controller.

The above-described examples can be used to detect apnea patients in a remote setting or track apnea in real-time.

The various examples described herein can be implemented on the ILR ASIC and/or integrated in other devices (e.g., the therapy device directly).

Although described with reference to an ILR, the presently-described examples can be used in other implanted measurement systems (e.g., ICD/CRT) or other surface measurement systems.

Figure 2:
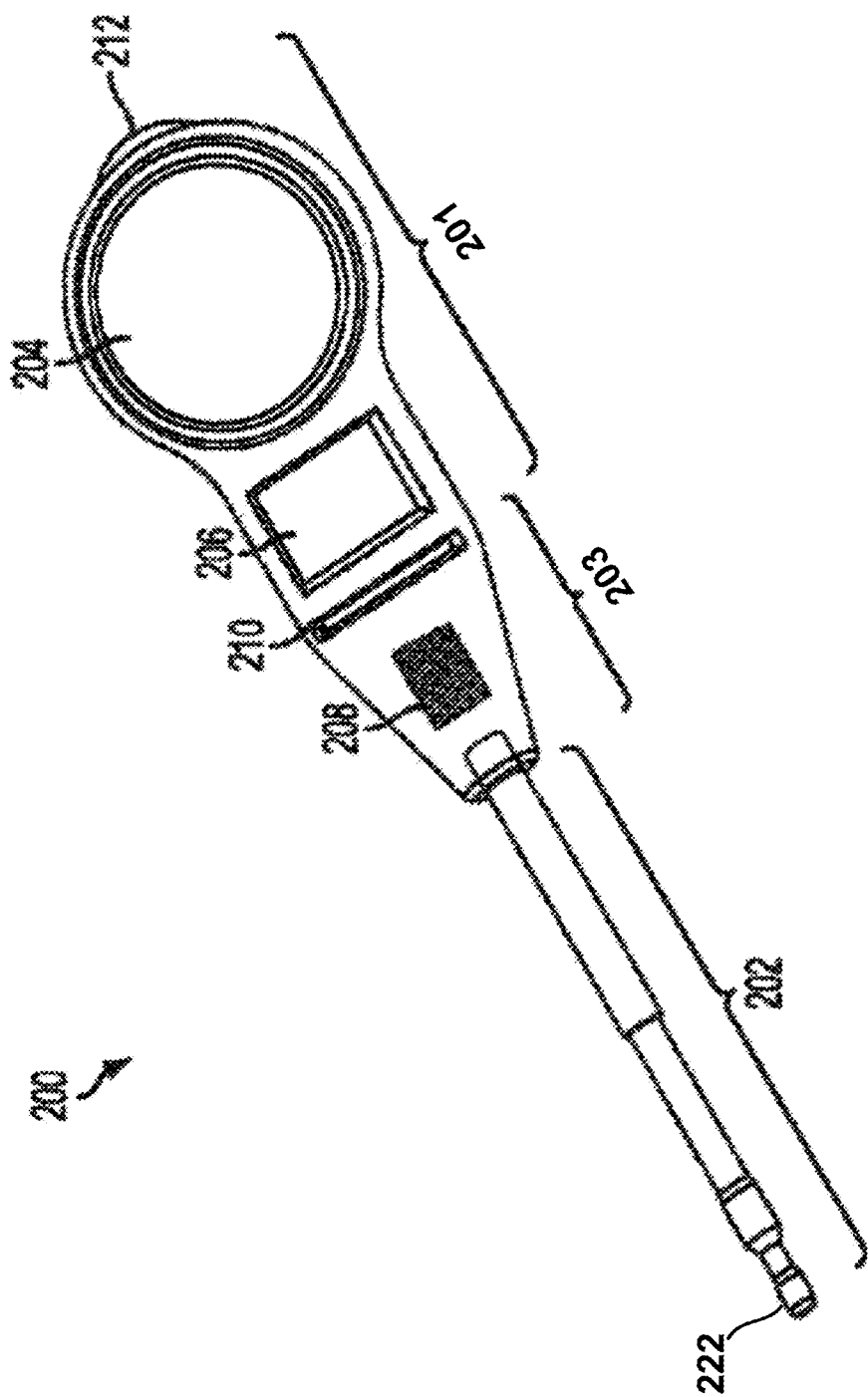
FIG. 2 is a perspective of another representative implantable device that can be subcutaneously implanted under a patient's skin.

Two representative examples of an implantable monitoring device are illustrated in FIGS. 1 and 2. Each of the implantable devices illustrated in FIGS. 1 and 2 is configured to record an electrical physiologic signal, such as an electrocardiogram signal for the patient, from which various diagnostic information including respiratory information can be derived. Thus, the devices described comprise waveform acquisition apparatuses. The description that follows will focus without limitation on implementations where the device 100/200 is used to monitor a subcutaneous ECG signal, but in other implementations such monitoring could be combined with or substituted by other monitoring functions.

FIG. 1 illustrates a representative implantable device 100 that can be subcutaneously implanted under a patient's skin, typically in a pectoral region of a patient's thorax, in accordance with various embodiments. The device 100 may be a minimally invasive implantable monitoring device that senses and records a physiologic parameter, such as electrical activity of the heart, within a body of a patient. In some implementations, the device 100 is an implantable monitoring device that senses and records a physiologic parameter, such as the ECG signal, within the body of the patient and wirelessly transmits information associated with the physiologic parameter to an external device or system. Such a monitoring-only device that records cardiac electrical information may be implanted in a human patient for a relatively short period of time, such as a few months for example.

The implantable device 100 shown in FIG. 1 includes a proximal section 102 and a distal section 103. The proximal section 102 includes a housing 104 within which various components of the device 100 are disposed, including electronic circuitry 120 (such as an analyzer, data acquisition module, etc.) and a battery 105, which may be single-use or rechargeable in various implementations. The housing 104 may be configured to include one or more electrodes, an example of which is shown as electrode 122. All or a portion of the housing 104 may be configured as an "active can," and may further include an indifferent electrode (not shown) which is electrically isolated from the housing electrode(s) 122. A header 106 is connected to the housing 104 and to a distal extension 110, which is generally flexible or shapeable. A distal electrode 112 is disposed at a distal end of the extension 110. The header 106 serves to electrically couple the distal electrode 112 and any other electrical or optical component of the distal extension 110 with components within the housing 104 (e.g., electronic circuitry 120). An antenna 108 is shown extending from the housing 104 and into the header. The antenna 108 is configured for telemetering data from the implantable device 100, and can be configured to effect bi-directional wireless communication with a patient-external device or system. In some embodiments, the antenna 108 can be incorporated into the distal extension 110.

FIG. 2 illustrates a representative implantable device 200 that can be subcutaneously implanted under a patient's skin, typically in a pectoral region of a patient's thorax, in accordance with other embodiments. The representative device 200 generally includes three sections: a proximal section 201, a distal extension 202, and a midsection 203 between the proximal section 201 and the distal extension 202. The proximal section 201 is configured to hermetically house a battery 204, which may be single-use or rechargeable in various implementations, and electronic circuitry 206 (e.g., an electronics module, analyzer, data acquisition module, etc.) for performing actions consistent with the device's intended purpose. Without limitation, examples of actions that may be performed with some implementations of the device 200 include measuring one or more physiologic signals, storing the measured signal(s) in memory within the device 200, processing and analyzing collected data, and wirelessly transmitting or receiving information to/from an external device, among others.

The midsection 203 may include a non-hermetic external surface, and may be designed to enclose or embed components suited for housing in a non-conductive enclosure, such as components that communicate by field or wave properties that may otherwise be impeded by a conductive housing. In this implementation, the midsection 203 houses an antenna 208 for wirelessly transmitting data to an external device or wirelessly receiving data from an external device. In some implementations, the midsection 203 can include a charging coil (not shown) that can be excited (e.g., with an external charging coil placed in proximity to the implant location) to recharge a rechargeable battery 204 of the device 200. Hermetic feedthroughs 210 may be provided where electrical connections enter or exit the hermetic proximal section 201 from the non-hermetic midsection 203 to maintain hermeticity of the proximal section 201.

The distal extension 202 may be a flexible subcutaneous lead attached to the midsection 203 at one end. Lead 202 may include one or more electrodes, such as distal electrode 222, for measuring electrical activity or stimulating body tissue. In some implementations, the distal extension 202 can serve as the telemetry antenna for the device 200, and in these cases the depicted antenna 208 may be omitted. In some implementations, the telemetry antenna function is incorporated into the distal extension (lead) 202 independent from any ECG sensing lead functionality. The device 200 may include a feature on an exterior surface to facilitate grasping of the device 200 during extraction. For example, a retraction loop 212 near the proximal end section 201 of the device 200 may be grasped or hooked in this fashion for ease of retraction. The loop 212 may in addition, or in the alternative, be configured as a suture hole to facilitate anchoring of the device 200 via a suture.

The devices 100 and 200 shown in FIGS. 1 and 2 may include one or more electrodes for electrically interfacing to surrounding tissue for the purpose of sensing electrical activity. In some implementations, devices 100 and 200 include two electrodes, such as a proximal electrode and a distal electrode, and may measure a potential difference (e.g., a subcutaneous ECG signal) between the proximal and distal electrodes. The electrodes may be located on the devices 100 and 200 to increase (e.g., maximize) signal vector length of a measured physiologic signal. In general, measured amplitude of a sensed physiologic signal, such as an ECG signal, will vary with device placement and orientation within the patient. Sensed signal amplitude may also be related to separation distance between the measuring electrodes. Positioning the proximal and distal electrodes near opposing ends (e.g., near opposite longitudinal ends) of the devices 100 and 200 can increase (e.g., maximize) the amplitude of the sensed physiologic signal for a given device length, which may lead to better measurement results. In other implementations, the devices 100 and 200 can include three electrodes, though any suitable number (one, two, three, four, five, etc.) may be used in other implementations. In some implementations, one or more of the electrodes of the devices 100 and 200 may comprise excitation electrodes or combination excitation/sense electrodes. By way of example, the devices 100 and 200 may measure a bio-impedance for diagnostic purposes by injecting a known current between two electrodes and measuring a resulting voltage between two electrodes.

Figure 3:
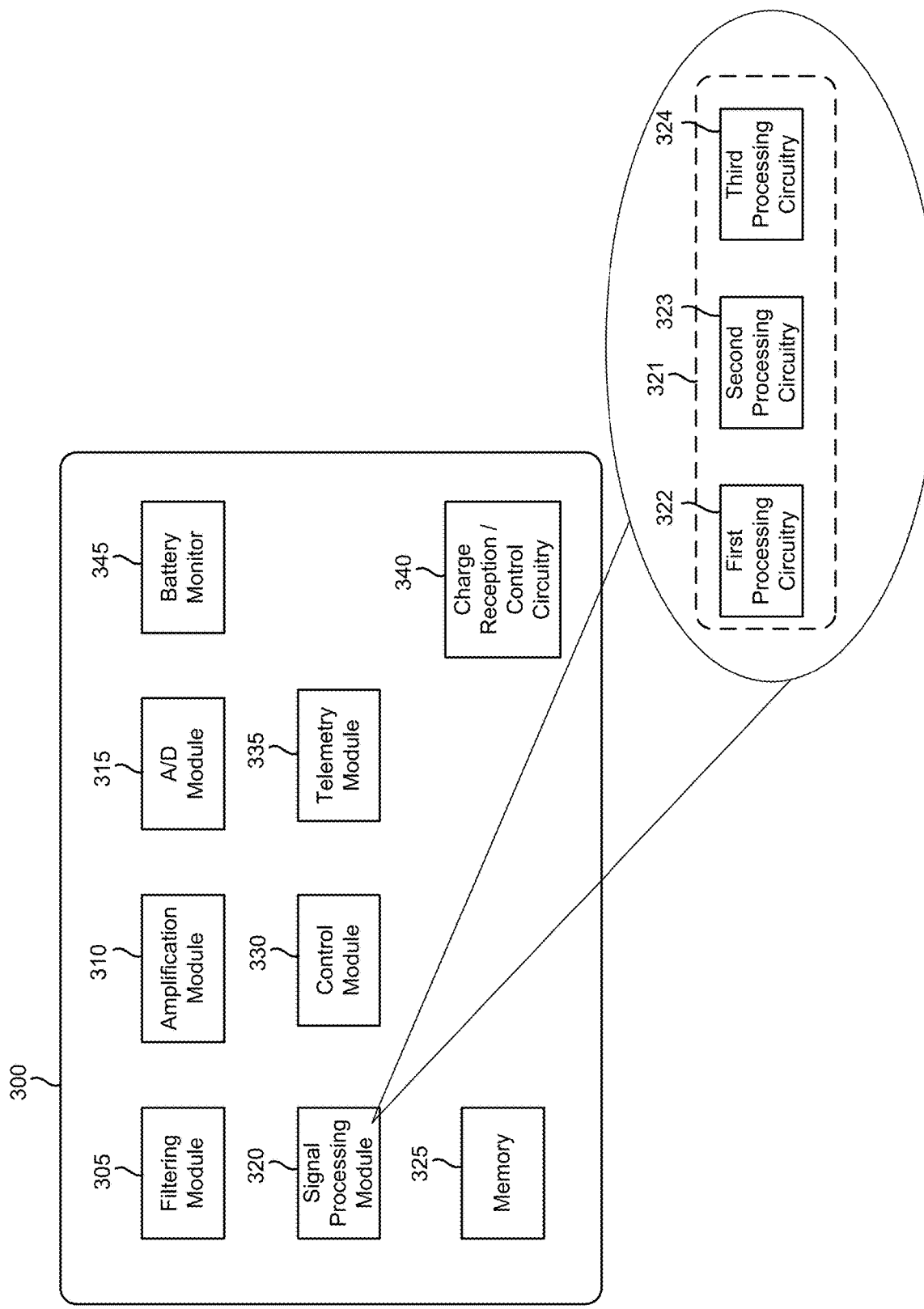
FIG. 3 is a block diagram of circuitry that may be included in implementations of a device used for respiratory monitoring.

FIG. 3 is a block diagram of circuitry 300 that may be included in implementations of an implantable device disclosed herein. In some implementations, the circuitry 300 or a portion thereof may be included in the electronics circuitry shown in various preceding figures. Components, modules, or circuitry may be combined or separated as desired, and may be positioned in one or more portions of the implanted device. A filtering module 305 may receive a sensed physiologic signal and appropriately filter the signal to remove unwanted noise or to pare the received signal to information in a desired frequency range, or above or below a desired frequency threshold. An amplification module 310 may amplify the received signal for processing, and an analog-to-digital converter 315 may convert the analog signal to a digital signal. The digital signal may be stored directly into memory 325, or may first be processed by a signal processing module 320. Signal processing module 320 may include functions to extract information from the measured signal, or to compress the measured signal to reduce the volume of data to store and transmit. In some embodiments, the signal processing module 320 includes signal acquisition and analysis capability. For example, the signal processing module 320 can include an analyzer 321. The analyzer module 321 can have a first processing circuitry 322, a second processing circuitry 323, and a third processing circuitry 324 in some embodiments. In some instances, the first processing circuitry 322 derives one or more respiratory disturbance indices from the physiological signal and detects if the one or more respiratory disturbance indices exceed a threshold value. The second processing circuitry 323 interpolates the one or more respiratory disturbance indices between adjacent time separated detection windows. The third processing circuitry 324 declares a respiratory disturbance episode based on the detected respiratory disturbance state during the detection windows and the interpolation between detection windows.

Memory 325 may include both volatile and non-volatile memory, according to various implementations, and may additionally store instructions that can be executed by a processor or logic device to perform specified actions.

A control module 330 may provide overall device control, and may include one or more processors that can execute instructions in response perform actions. A telemetry module 335 may be used, in conjunction with the telemetry antenna, for communication with an external device. Charge reception/control circuitry 340 may optionally be used in implementations that include a rechargeable battery to control reception of charge energy over a charge reception apparatus and coordinate recharging of the battery. A battery monitoring module 345 may provide one or more of controlling the charge current/voltage as appropriate for the type of battery, providing data that can be transmitted to a charger during charging to control and terminate charge time, assess a state of the battery from charge to depletion via voltage, impedance, charge-counting or other means, provide data to communicate to an external device for feedback as to when to charge or if an early charge is required. For simplicity, connections between the various modules are not shown in FIG. 3.

Figure 4:
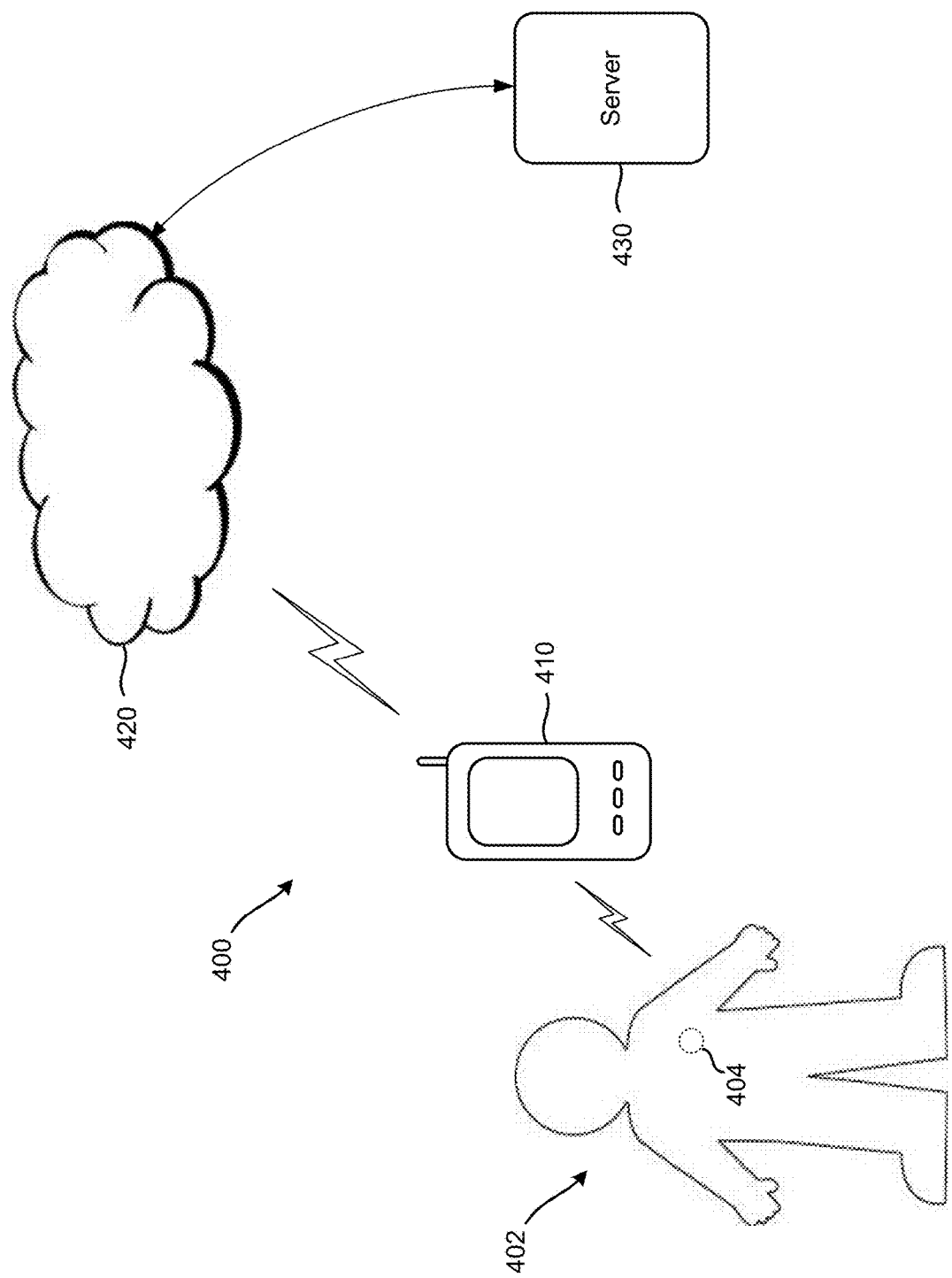
FIG. 4 is a diagram of a representative system used for respiratory monitoring.

FIG. 4 is a diagram of a representative system 400 in accordance with various embodiments. A sleep disorder monitoring device of a type disclosed herein can be embodied in an implantable device (e.g., subcutaneous extra-thoracic device, intra-thoracic device), a cutaneous patient-external device, or a hybrid device having both patient-internal and patient-external components. A sleep disorder monitoring device of a type disclosed herein can be incorporated in a variety of system implementations, a representative example of which is shown in FIG. 4. The system 400 includes a patient monitoring device 404 implanted in a body of a patient 402. The device 404 may correspond to any of the patient monitoring devices disclosed herein. When implanted, the device 404 may collect physiological data from the patient 402. A handheld computing device 410 may be programmed to communicate wirelessly (e.g., transmit or receive data via radio frequency telemetry) with the implantable device 404. In some implementations, an external charging device (not shown) may be used to periodically recharge a battery of the implantable device 404, though the device 404 may alternatively use a single-use battery in some implementations.

In various implementations, the patient 402 may use the handheld device 410 to manually initiate data collection by the device 404 (e.g., initiate ECG signal sensing and recording) such as prior to beginning a sleep cycle (e.g., initiate ECG signal sensing and recording). For example, if the patient 402 feels drowsy, she may press a button on the handheld device 410, and the handheld device 410 may wirelessly command the device 404 to record and store physiologic data. The device 404 may also record a physiologic signal when it determines that such recordation may provide useful information. For example, the device 404 may monitor a physiologic parameter (e.g., respiration), and may record an ECG signal based on predetermined characteristics of the physiologic parameter. In some implementations, the device 404 may periodically record sensed physiologic information according to a predetermined schedule. For example, the device may record a strip of data (e.g., covering a predetermined number of heart beats or having a predetermined strip duration or length) once every minute, every several minutes, every hour, every several hours, every day, every several days, etc.

The device 404 may periodically transmit collected data to the handheld device 410, such as every few minutes, hours or once per day, for example. In some implementations, the device 404 may transmit sensed data in real time to the handheld device 410, and the handheld device 410 may store the data in internal memory or display the data as a waveform or otherwise on a display screen of the handheld device 410. The handheld device 410 is configured to wirelessly communicate with the cloud 420 (e.g., the Internet) via a cellular or Wi-Fi connection, and to establish a connection with a remote server 430. The handheld device 410 may send and receive data to/from the server 430. In some embodiments, the handheld device 410 may transmit data through the cloud 420 and to the remote server 430, where the data may be processed and analyzed automatically (e.g., algorithmically by the server 430) and/or by a physician or a health care provider. Thresholds can be computed at the server 430 and transmitted to handheld device 410 for upload to the device 404. In some implementations, data analysis may occur within one or both of the device 404 and the handheld device 410 (or in a distributed manner between two or more of these components). Data analysis can include detection of cardiac, musculature, neural, and sleep anomalies based on the collected data and trending of such detection data. Data analysis can include detection of respiratory anomalies based on the collected data and analysis (e.g. trending) of such detection data.

FIGS. 1-4 describe exemplary systems and devices for disordered breathing detection and monitoring. According to some embodiments, the systems can include a waveform acquisition apparatus (e.g., device 100/200) that is operable to detect a physiological signal during discrete time separated detection windows and an analyzer (either on the device or remote therefrom). The analyzer includes first processing circuitry that derives one or more respiratory disturbance indices from the physiological signal and detects if the one or more respiratory disturbance indices exceed a threshold value. The analyzer also includes second processing circuitry that interpolates the one or more respiratory disturbance indices between adjacent time separated detection windows. Additionally, the analyzer includes third processing circuitry that declares a respiratory disturbance episode based on the detected respiratory disturbance state during the detection windows and the interpolation between detection windows.

In some embodiments, the methods, systems, and apparatuses described can provide for both a clinician set mode of operation and a patient set sleep mode of operation. The patient set sleep mode of operation decreases the duration of time between the discrete time separated detection windows for increased data capture. Additionally or alternatively, the patient set sleep mode of operation may increase the number of instances of data transmission (i.e. the frequency of transmission) from the device as compared to the clinician set mode.

Figure 5:
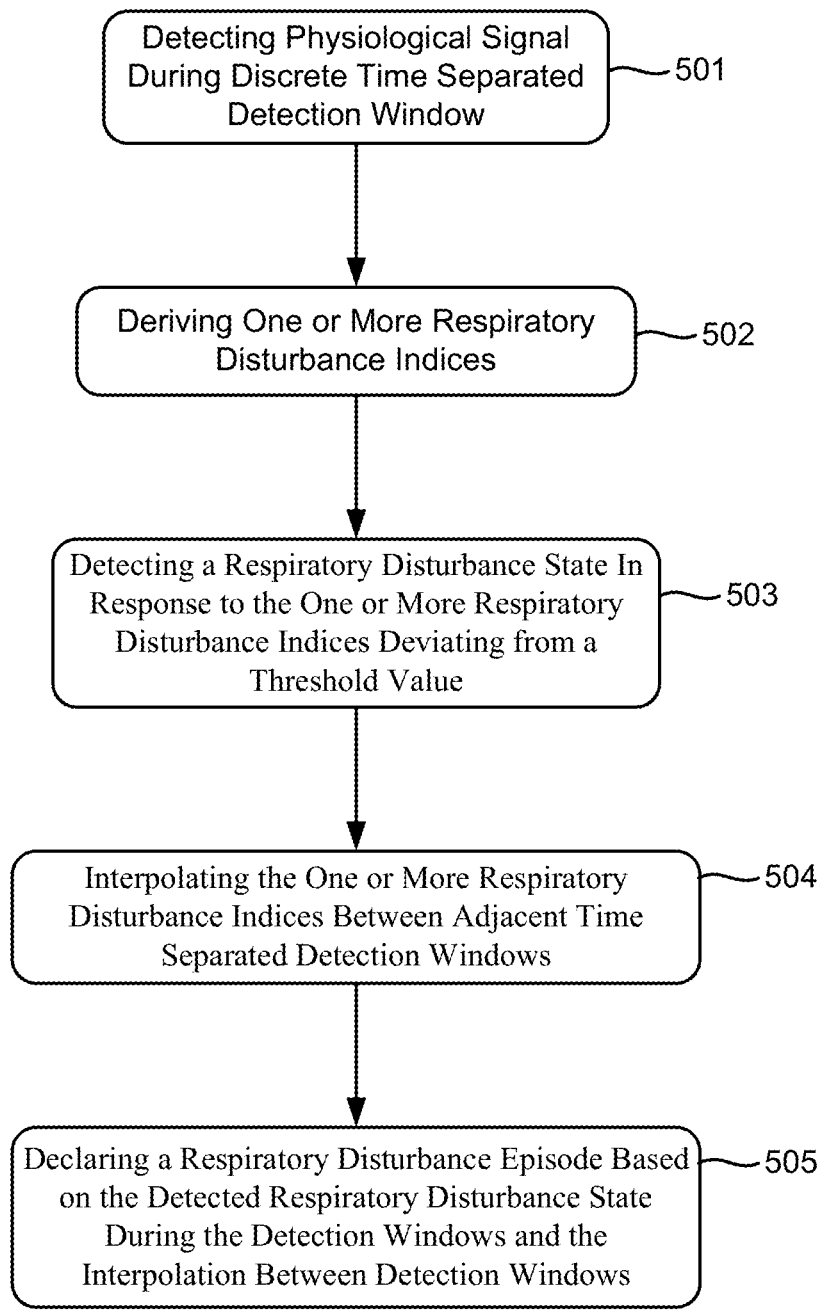
FIG. 5 is a flow diagram of a method of detecting disordered breathing according to one embodiment.

FIG. 5 shows a flow diagram of a method of detecting disordered breathing according to one embodiment. The method detects 501 a physiological signal during discrete time separated detection windows. One or more respiratory disturbance indices are derived 502 from the physiological signal. A respiratory disturbance state is detected 503 in response to the one or more respiratory disturbance indices deviating from a threshold value. The method interpolates 504 one or more respiratory disturbance indices between adjacent time separated detection windows. The method can declare 505 a respiratory disturbance episode based on the detected respiratory disturbance state during the detection windows and the interpolation between detection windows.

Figure 6:
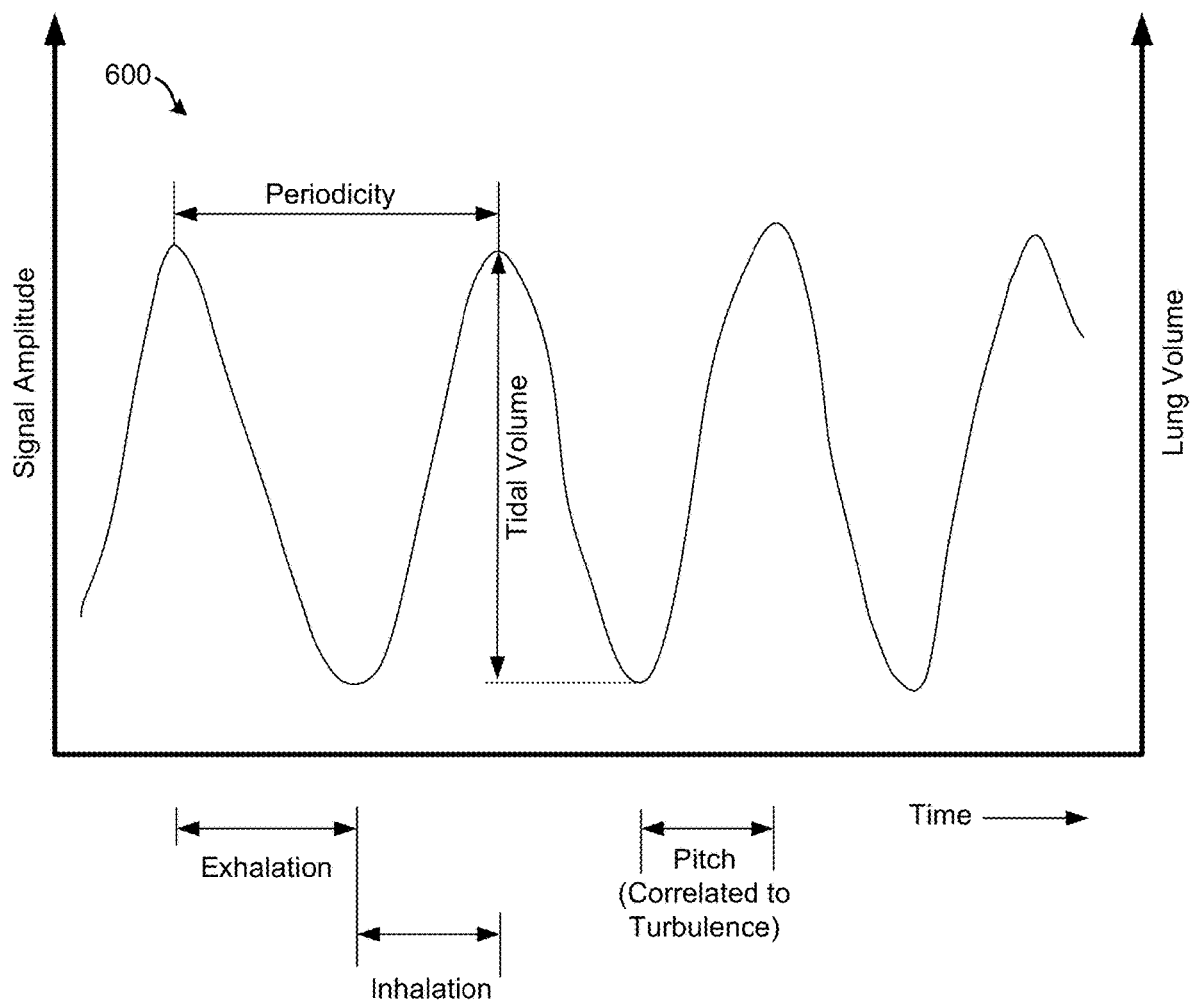
FIG. 6 illustrates normal respiration waveform as represented by a signal produced by one or more sensors.

FIG. 6 illustrates normal respiration waveform as represented by a signal 600 produced by one or more sensors. As illustrated in FIG. 6, individual breaths are comprised of inhalation and exhalation, which can be sensed and characteristics of the signal measured. During non-REM (non-Rapid Eye Movement) sleep, a normal respiration pattern includes regular, rhythmic inhalation-exhalation cycles without substantial interruptions. These rhythmic cycles have a periodicity (measure of the time duration between signal peaks or valleys) that can be measured as indicative of a respiration rate. A tidal volume of the signal can also be measured and can comprise a peak-to-valley amplitude change in the signal (i.e. a measure of magnitude). Thus, tidal volume represents the normal volume of air displaced between normal inhalation and exhalation when extra effort is not applied.

Low pass filtering on the ECG signal can be performed to isolate the breathing component. Additionally or alternatively, high pass filtering can be performed on the ECG signal to isolate the high frequency component of the EMG (muscle noise, costal muscles or pectoral). These filtering and other signal processing techniques could be done singularly or in combination to derive the breathing signal that will be processed to determine the intensity, periodicity, power, etc. of a patient's breathing in order to detect sleep disordered breathing.

Episodes of disordered breathing may be detected by monitoring the respiratory waveform for various respiratory disturbance indices (e.g., tidal volume intensity, periodicity, turbulence, signal power, duration, etc.) deviating from a threshold value. For example, when the tidal volume of the patient's respiration, as indicated by the measured signal, falls below the threshold value, the respiratory disturbance state (e.g., a hypopnea and/or apnea state) is detected. In other embodiments, if the periodicity of the patient's respiration increases above or decrease below a respiratory disturbance state threshold value, a respiratory disturbance state (e.g., an apnea event) is detected. For example, an apnea event can be detected if a non-breathing period (i.e., a period without inhalation) exceeds a predetermined time period.

In yet other embodiments, the vigorous inhalation and exhalation associated with some disordered breathing conditions can be used to identify a respiratory disturbance state. For example, an apnea state can have a higher mean frequency (pitch) than normal breathing. Similarly, the apnea state can have a more vigorous exhalation with a higher mean frequency (pitch) than normal breathing. This more vigorous inhalation/exhalation can generate turbulence in the air flowing through the patient's airway. Thus, the pitch of the respiration waveform can be indicative of a respiratory disturbance state in some instances. Turbulence (pitch) can be measured by, for example, an EMG signal of muscle activity.

The threshold value can comprise one or more of a standard deviation from what is considered a normal respiratory index value where a respiratory disturbance is not present, a variance from what is considered a normal respiratory index value where a respiratory disturbance is not present, a personalized change what is considered a normal respiratory index value where a respiratory disturbance is not present, a variance from what is considered a normal respiratory index value where a respiratory disturbance is not present, a normalized index, a physician set index, a percentage change of a preceding value, an absolute change, a relative change, an adaptive threshold, an AHI score or derivative thereof, etc.

FIGS. 7A-7E show various exemplary sleep disordered respiration waveforms as represented by a signal such as an EMG derived from the one or more sensors. As illustrated the FIGS. 7A-7E, a respiratory disturbance episode can be based on a detected respiratory disturbance state during one or more detection windows and the interpolation between detection windows (to be discussed subsequently).

Figure 7A:
FIGS. 7A-7E each show a waveform of respiratory disturbance state during a single detection window.
Figure 7B:
Figure 7C:
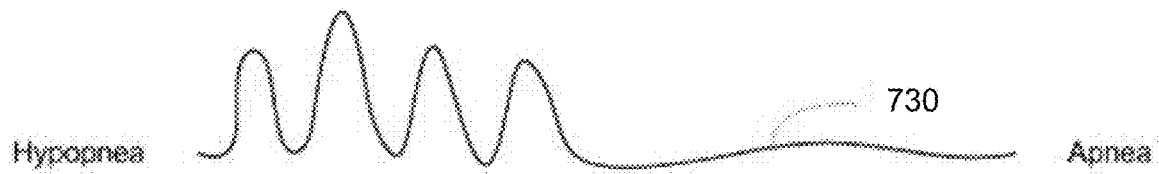
Figure 7D:
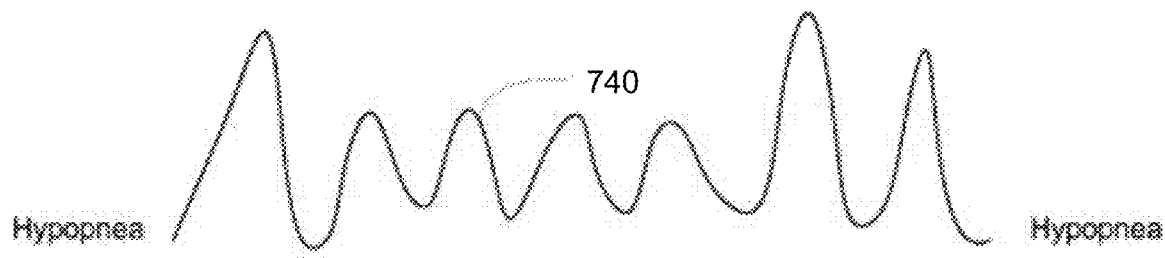
Figure 7E:
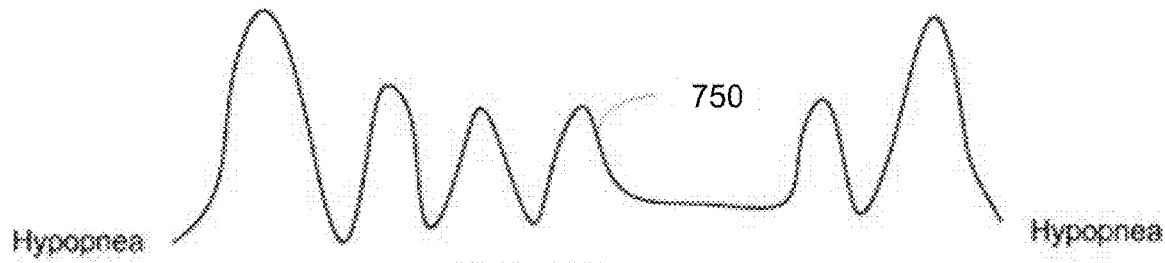

Each of FIGS. 7A-7E show a respiratory disturbance state during a single detection window. The detected respiratory disturbance states are not static in nature but can alternate between various respiration types in some cases. Thus, the sensed respiratory disturbance states can include an apnea-apnea respiration cycle 710 (FIG. 7A), a hypopnea-hypopnea respiration cycle 740 (FIG. 7D) and 750 (FIG. 7E), and a mixture of hypopnea and apnea respiration cycles 720 (FIG. 7B) and 730 (FIG. 7C). Other state transitions are possible but not specifically described herein. Although not illustrated, the sensed respiratory disturbance states can also include a normal respiration cycle (FIG. 6) that transitions to a disordered cycle.

Figure 8A:
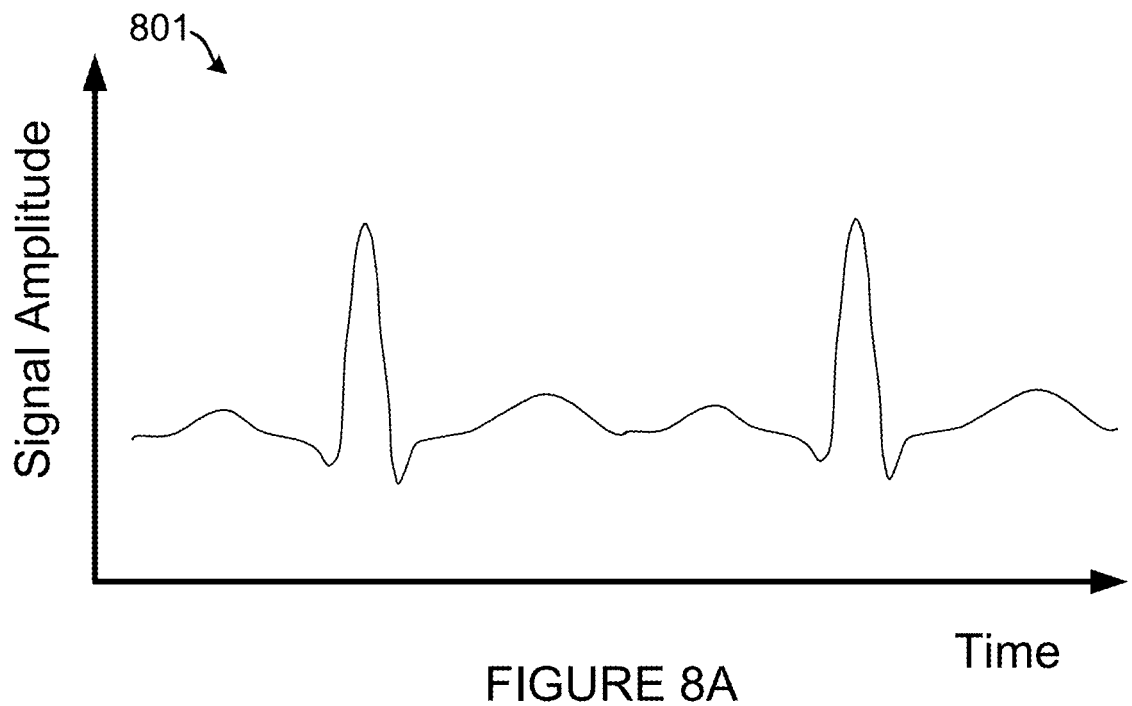
FIG. 8A shows a sample ECG signal waveform.

FIG. 8A shows a sample ECG signal waveform 801 captured from a device such as a Holter monitor or ILR. The ECG signal captures body electrical activity including heart activity and muscle activity. Indeed, EMG (muscle activity) can be derived from the ECG signal as described in U.S. Pat. No. 8,180,442 and United States Patent Application Publication 2007/0032733A1, the disclosures of which are incorporated by reference herein. Using a signal separation (e.g., frequency domain filtering or wavelet decomposition), the measured ECG signal can be split into several components. The high frequency components may correspond to muscle activity (e.g., respiratory upper-chest movement). Thus, respiratory derived EMG signal components as well as ECG signal components (cardiac activity) can be used to determine the presence of and quantify patient disordered breathing events.

As discussed previously, in some embodiments, the quantification and detection of patient activity can be performed on the periodic, asymptomatic, or symptomatic ECG strips acquired during normal ILR operation or extended to the measured ECG in real-time for all time instances.

Figure 8B:
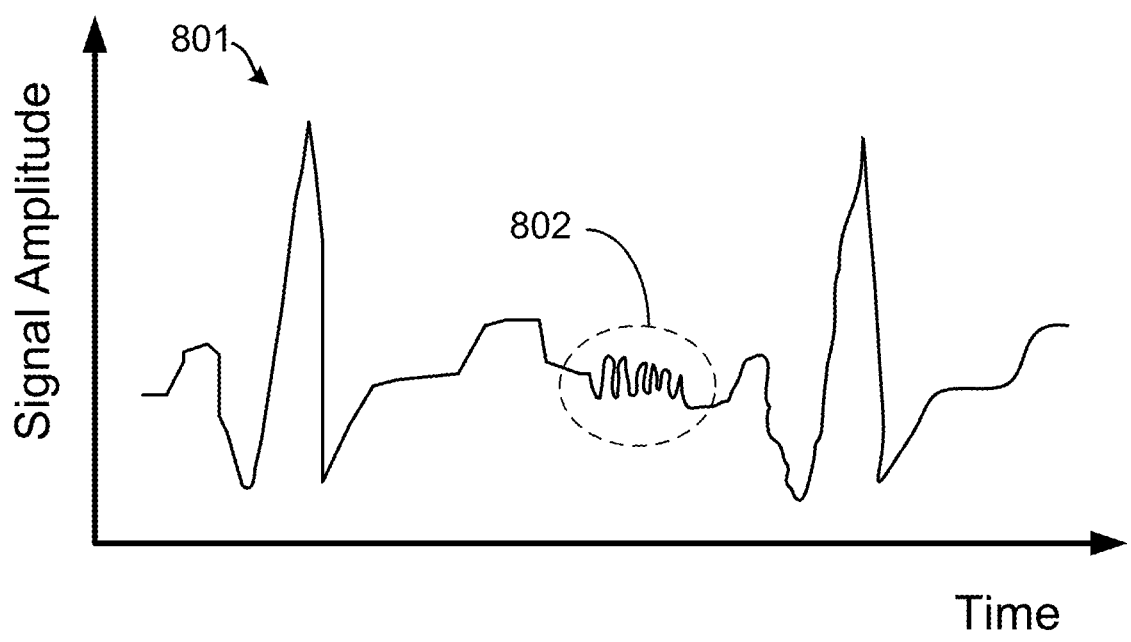
FIG. 8B shows an exaggerated example of an ECG derived EMG signal with an exaggerated disordered breathing event.

FIG. 8B shows an exaggerated example of an ECG derived EMG signal 801 with an exaggerated disordered breathing event 802. The system may detect relatively subtle changes in muscle activity by establishing, for example, a normal amplitude level of inter-ECG beat signal, such as by way of sampling inter-breath amplitude levels and detecting a running average level of intermediate QRS signal levels. Residual EMG signals are increased when compared to the normal or average base-line EMG and may suggest elevated breathing effort from either intercostal muscles located between the ribs or the lower abdominal muscles.

In some instances, the disordered breathing event 802 can be related to an obstructive sleep apnea event or a central sleep apnea event. Real-time derivation of EMG from ECG or superimposition of ECG on EMG may be extracted to compute breathing effort related EMG changes. Techniques described can be used to distinguish between obstructive sleep apnea versus central sleep apnea. In particular, a capability to record broadband ECG being for example DC (or 0.01 Hz ECG high pass value) to 200 Hz or more, may provide a means to gate out conventional QRS pulses and enable sensitive measurement of residual muscle signal. Muscle signal may reflect use of abdominal or thoracic muscles as may be evident during obstructive sleep apnea, where the subject's upper airway palette typically has collapsed but autonomic or involuntary breathing effort continues, despite collapse of the upper airway. In contrast central sleep apnea is not accompanied with breathing effort as breathing is prevented due to cessation of involuntary (or automatic) neural driving mechanism. An analyzer running processing circuitry as described variously in reference to FIGS. 1-4 can be used to analyze various characteristics of both the ECG signal and the EMG signal. These signals can be analyzed alone or in tandem in some cases to increase the likelihood of identifying disordered breathing events. Phase synchronizations between the ECG and the EMG signals may be determined by evaluating relationships between the respiratory signal (discussed in reference to FIGS. 6 and 7A-7E) and the heart rate period in terms of power spectra and phase relations. Evaluation can include mutual derivation (both linear and non-linear), correlation, statistical analysis, and other known techniques as a measure of coupling between cardiac function and respiratory function.

Cardiac events that can be related to disordered breathing can be gathered including absolute heart rate (e.g., as measured by RR interval time series, RR consecutive difference time series, etc.), changes in heart rhythm, and/or changes in cardiac response to autonomic regulation, such as cardio-acceleration/cardio-deceleration, existence of arrhythmia(s) (e.g. premature atrial complexes (PACs), P-wave variability), etc. Such cardiac events, if sensed or interpolated, can be correlated with one or more respiratory disturbance indices used when declaring a respiratory disturbance state and/or a respiratory disturbance episode.

Additionally or alternatively, the EMG signal can be analyzed and one or more respiratory disturbance indices related to respiration can be extracted and used when declaring a respiratory disturbance state and/or a respiratory disturbance episode.

FIG. 9 provides an example of a changing disordered breathing state captured by a sequence of time separated data strips 901, 902, 903, and 904. The data strips 901, 902, 903, and 904 can be one or more of three types: symptomatic, asymptomatic, and trending. In some examples, trending data strips are basically fixed duration recordings (but the duration can be changed dynamically) that happen at regular intervals, for instance, every 7.5 minutes, 15 minutes, 4 hours, etc., based on user setting. The data strips 901, 902, 903, and 904 are time separated from one another, and thus, are captured during discrete time separated detection windows. The individual strips 901, 902, 903, and 904 can be analyzed, on an ILR or on a PDM or offline on servers, for apnea or other disordered breathing activity.

Many processing methods can be used to analyze the strips, only several analysis methods are described herein. For example, if the objective is to detect disordered breathing with retrospective data, the trending data can be time ordered and analyzed in two ways. Starting with the first trending strip 901, an algorithm or manual reader can track one or more respiratory disturbance indices 911, 912, 913, and 914 corresponding to each strip 901, 902, 903, and 904, respectively. The algorithm or manual reader can retain the ending state (which may or may not be a disordered breathing state). During the tracking period of each strip 901, 902, 903, and 904, if the one or more respiratory disturbance indices 911, 912, 913, and 914 exceed the threshold value, the respiratory disturbance state is detected. In some instances, the gathered data from each strip 901, 902, 903, and 904 can include information related to the one or more respiratory disturbance indices 911, 912, 913, and 914 and can be stored for analysis and/or presentation. By way of example, the analysis can simply be to record the number of instances where a respiratory disturbance state is detected for each strip over a number of strips and present this data in a histogram type display. In some cases, all sensor signals can be captured, or only the ones where apnea or another disordered breathing was detected. In other embodiments, attributes (e.g., intensity, amplitude, periodicity, power, turbulence, etc.) of interest that can comprise or be related to the one or more respiratory disturbance indices can be dynamically measured and analyzed. These attributes can be processed in real-time or can be derived off-line (e.g. a remote setting) as desired and the respiratory disturbance state(s) detected and/or presented if the one or more respiratory disturbance indices exceed the threshold value.

FIG. 9 illustrates that for the next strip, the beginning condition of the one or more respiratory disturbance indices 911, 912, 913, and 914 can be set to the end condition of the previous strip. This can be done by, for example, a sample-and-hold device, storing the gathered data including the one or more respiratory disturbance indices from the prior sample for use in comparison, etc. Thus, the trending data technique interpolates the one or more respiratory disturbance indices 911, 912, 913, and 914 between an ending state and a beginning state of the adjacent time separated detection windows. With each new strip, the algorithm or manual reader can track the one or more respiratory disturbance indices 911, 912, 913, and 914 for the strip duration. During the tracking period, (the duration of the strips 901, 902, 903, and 904) if the one or more respiratory disturbance indices 911, 912, 913, and 914 exceed the threshold value, the respiratory disturbance state can be detected and declared. The technique described can be used to detect apnea and other disordered breathing conditions in patients in a remote setting or can be used to track apnea and other disordered breathing conditions in real-time. In some cases, the respiratory disturbance episode can be declared based on the detected respiratory disturbance state during the detection windows (e.g., the strips 901, 902, 903, and 904) and the interpolation between detection windows.

Figure 10:
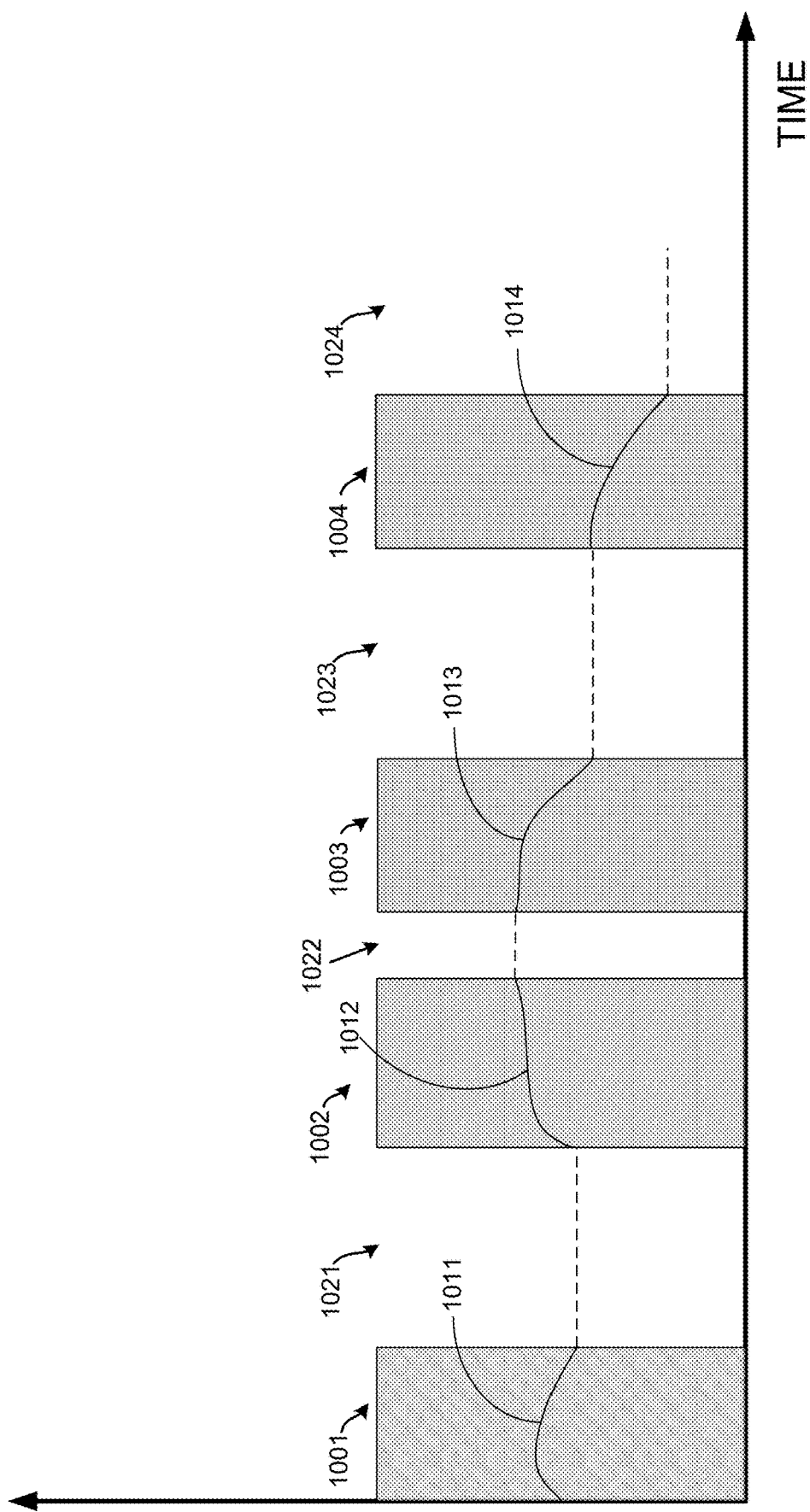
FIG. 10 is a graph showing a changing disordered breathing state such as an apnea state according to one embodiment.

FIG. 10 shows another example embodiment of a changing disordered breathing state captured by a sequence of data strips 1001, 1002, 1003, and 1004. The data strips 1001, 1002, 1003, and 1004 are captured and processed in the manner discussed in reference FIG. 9 to determine and track one or more respiratory disturbance indices 1011, 1012, 1013, and 1014 that correspond to each strip 1001, 1002, 1003, and 1004, respectively. However, in FIG. 10 the duration of intervals 1021, 1022, 1023, and 1024 are changed dynamically. Thus, the intervals between the time separated recordings can vary in duration. In some cases, the intervals between time separated recording can be changed algorithmically, (closed loop) when certain triggers of thresholds of sleep disorder are detected.

The intervals between time separated records could also be changed, for example, manually (open loop) by a physician or patient. In the open loop case, the separation between the time separated recordings is fixed and not dependent of the disease or breathing detections. In some cases, the technique could rely on interpolation and sample and hold comparisons.

An example of a closed loop case is illustrated in FIG. 10. In FIG. 10, the duration between time separated recordings can be dynamic and track the breathing disorder by altering the gap between recordings to give the physician or patient a better resolution to the detections.

FIG. 10 illustrates that when a disordered breathing state is identified, as indicated by one or more respiratory disturbance indices 1012 exceeding a threshold as at the ending state of the second data strip 1002, the duration 1022 between the second data strip 1002 and the third data strip 1003 can be reduced to aid in tracking the breathing disorder. During the third data strip 1003 the one or more respiratory disturbance indices 1013 are detected. If, as illustrated in FIG. 10, a normal breathing state has returned by the ending state of the third data strip 1003 the duration 1023 can revert back to a preset value or another value similar to the duration 1021.

Figure 11:
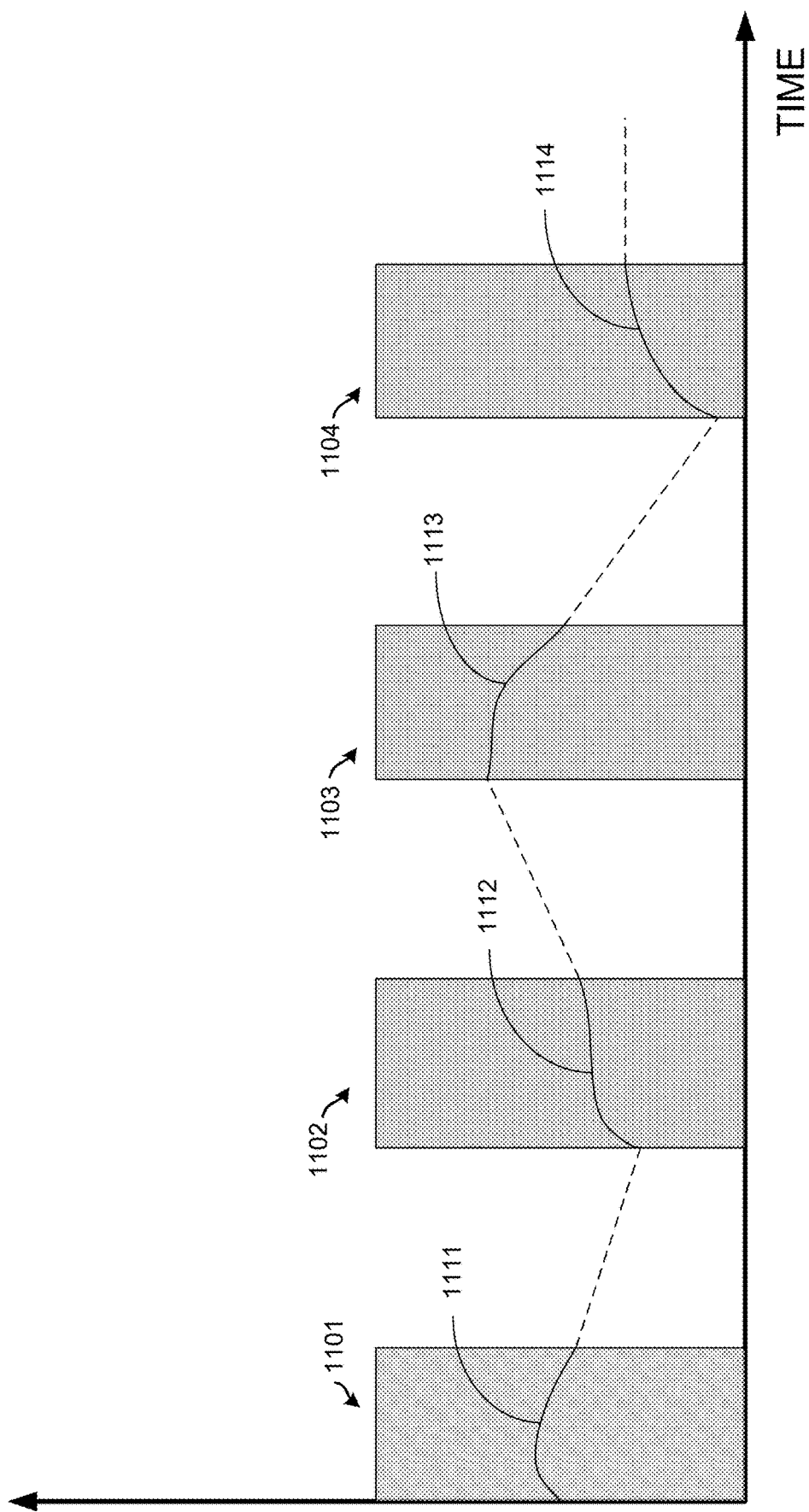
FIG. 11 is a graph showing a changing disordered breathing state such as an apnea state according to yet another embodiment.

FIG. 11 shows another example embodiment of a changing disordered breathing state captured by a sequence of time separated data strips 1101, 1102, 1103, and 1104. FIG. 11 illustrates that for each subsequent strip (e.g., 1102, 1103, and 1104), the initial condition of the one or more respiratory disturbance indices 1111, 1112, 1113, and 1114 can be generated again via algorithm or manual reader as was the case with the first strip 1101 or alternatively can be generated by other techniques including using trending of the prior one or more disturbance indices 1111, 1112, 1113, and 1114 as illustrated in FIG. 11. The initial condition of the one or more respiratory disturbance indices 1111, 1112, 1113, and 1114 may differ from the end state of the previous strip. Comparison can be made between one or more respiratory disturbance indices 1111, 1112, 1113, and 1114 at the ending state of the previous strip and the one or more respiratory disturbance indices at the initial state of the current strip for indications of disordered breathing (e.g. as indicated by a sudden jump or fall in the one or more respiratory disturbance indices as measured in real-time). Thus, the trending data technique interpolates the one or more respiratory disturbance indices 1111, 1112, 1113, and 1114 between an ending state and a beginning state of adjacent time separated detection windows. With each new strip, the algorithm or manual reader can track the one or more respiratory disturbance indices 1111, 1112, 1113, and 1114 for the strip duration. In some cases, a respiratory disturbance episode can be declared based on the detected respiratory disturbance state during the detection windows (e.g., the strips 1101, 1102, 1103, and 1104) and the interpolation between detection windows. The technique described can be used to detect apnea and other disordered breathing conditions in patients in a remote setting or can be used to track apnea and other disordered breathing conditions in real-time. In some cases, a respiratory disturbance episode can be declared based on the detected respiratory disturbance state during the detection windows (e.g., the strips 1101, 1102, 1103, and 1104) and the interpolation between detection windows.

In some embodiments, the respiratory disturbance episode is declared if the respiratory disturbance state is present in both an ending state and a beginning state of adjacent time separated detection windows. The respiratory disturbance episode is not declared if the respiratory disturbance state is not present at both the ending state and the beginning state of adjacent time separated detection windows.

In further embodiments, the data other than solely the one or more respiratory disturbance indices can be collected during adjacent time separated strips and can be interpolated as described in reference to FIGS. 9-11. Thus, one or more characteristics of heart activity and muscle activity can be captured and interpolated between an ending state and a beginning state of the adjacent time separated strips. These can be used for comparison between the adjacent time separated strips.

Interpolation can be based upon a variety of techniques and information. For example, interpolation can be based on physician entered non-parametric data in some cases. Additionally or alternatively, interpolation can be based on one or more pre-programed settings. In other cases, interpolation is based upon one or more of a standard deviation, a variance, a personalized change, a normalized index, a physician set index, a percentage change of a preceding value, an absolute change, a relative change, and an adaptive threshold. Interpolation can be based on a priori information regarding a patient wellness such as age, weight, known health conditions, measured blood pressure, sex, illness history, genetic disposition, time of data collection, subject sleep or wake state, coronary risk, respiratory risk, etc.). In yet other embodiments, interpolation can be based upon learned information regarding a patient wellness. Such information can be physician gathered and entered, patient gathered and entered, based upon learning algorithms, etc.

The threshold value can comprise one or more of a standard deviation from what is considered a normal respiratory index value where a respiratory disturbance is not present, a variance from what is considered a normal respiratory index value where a respiratory disturbance is not present, a personalized change what is considered a normal respiratory index value where a respiratory disturbance is not present, a variance from what is considered a normal respiratory index value where a respiratory disturbance is not present, a normalized index, a physician set index, a percentage change of a preceding value, an absolute change, a relative change, an adaptive threshold, an AHI score or derivative thereof, etc.

In some cases the threshold value can be triggered based on one or more of a threshold proportion of discrete time separated detection windows indicating the one or more respiratory disturbance indices has deviated from the threshold value, a trend in collected data indicating a statistically significant shift in the one or more respiratory disturbance indices toward deviation with the threshold value, and an AHI score or derivative thereof. In some implementations, the device 100/200 (FIGS. 1 and 2) such as an ILR can have the apnea detection on the ILR and perform a signal capture upon apnea detection (e.g., an apnea AHI score can be used as the threshold). In various examples, all sensor signals can be captured, or only the ones where apnea was detected.

Figure 12:
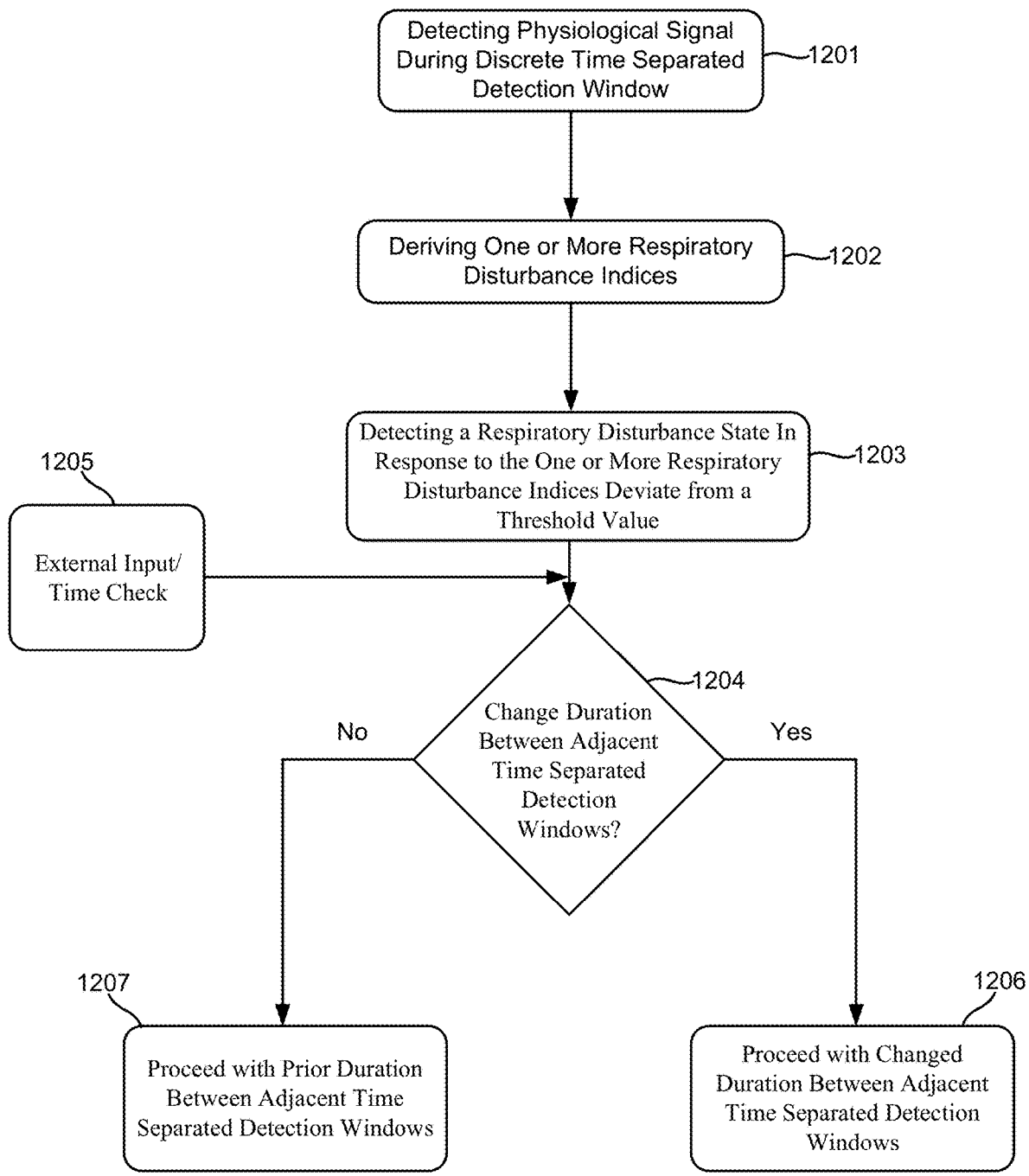
FIG. 12 is a flow diagram showing a potential change in the duration between adjacent time separated detection windows according to an open loop method.

FIG. 12 shows a flow diagram of a potential change in the duration between adjacent time separated detection windows according to an open loop method. A physiological signal is captured 1201 in discrete time separated detection windows and one or more respiratory disturbance indices are derived 1202 from the physiological signal. Based upon the one or more respiratory disturbance indices deviating from a threshold value a respiratory disturbance state can be declared 1203. At step 1204, a query is conducted to determine if the duration of between adjacent time separated detection windows should be changed. If, for example, input 1205 from a physician or patient indicates that a change in the duration is warranted, the method proceeds to step 1206. In other embodiments, input 1205 such as a time stamp indicating a nighttime, causes the method to proceed to step 1206. If no input 1205 (and/or daytime, etc.) is detected, the method proceeds to step 1207.

Figure 13:
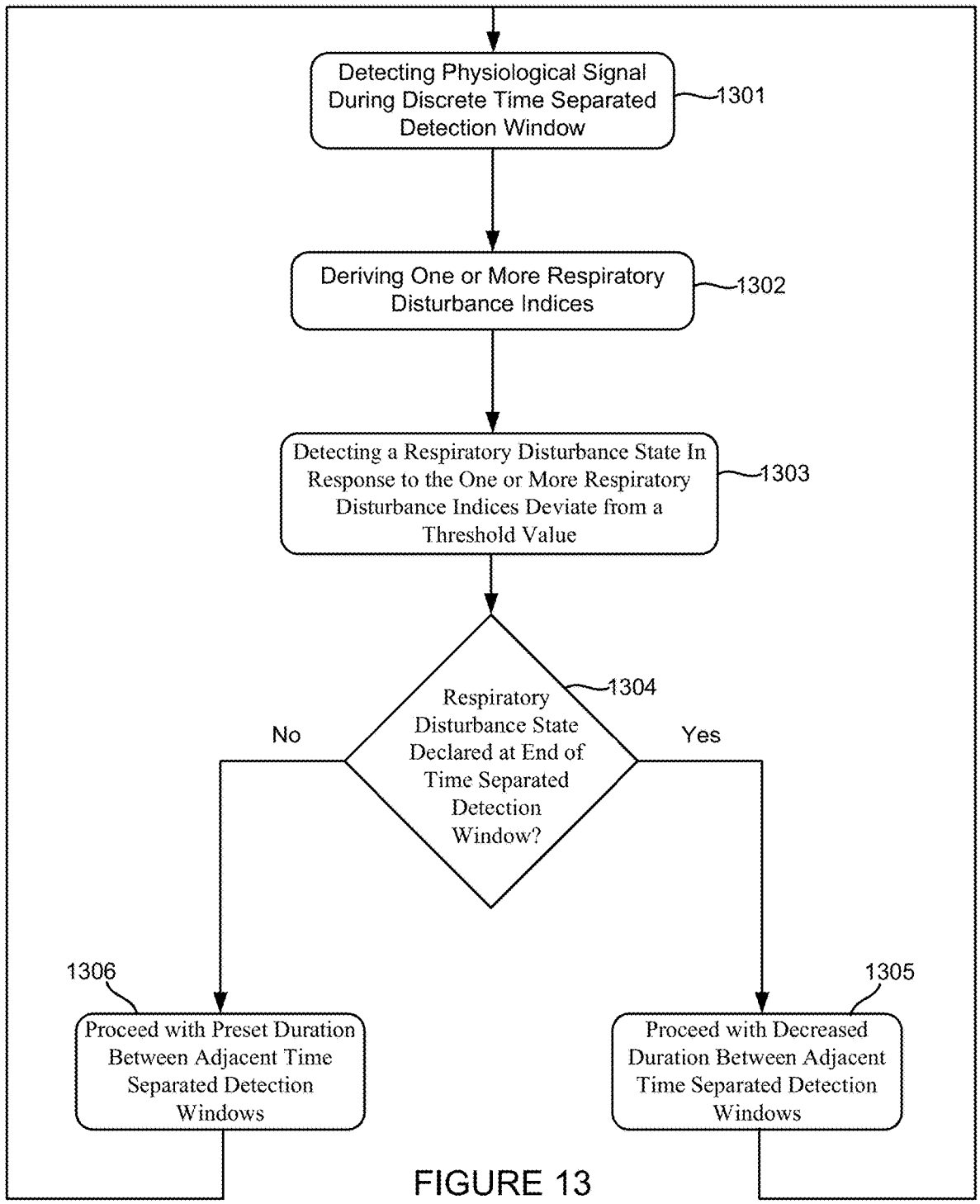
FIG. 13 is a flow diagram showing a potential change in the duration between adjacent time separated detection windows according to closed loop method.

FIG. 13 is a flow diagram showing a potential change in the duration between adjacent time separated detection windows according to closed loop method. A physiological signal is captured 1301 in discrete time separated detection windows and one or more respiratory disturbance indices are derived 1302 from the physiological signal. Based upon the one or more respiratory disturbance indices deviating from a threshold value a respiratory disturbance state can be declared 1303. At step 1304, if a respiratory disturbance state is declared at any point and/or at the end of one of the time separated detection windows, the method proceeds to step 1305, where the duration between the adjacent time separated detection windows is decreased. If no respiratory disturbance state is declared at any point and/or at the end of one of the time separated detection windows, the method proceeds to step 1306 causing a lengthening, continuation, return to preset levels, etc. of the time separated detection windows.

Figure 14:
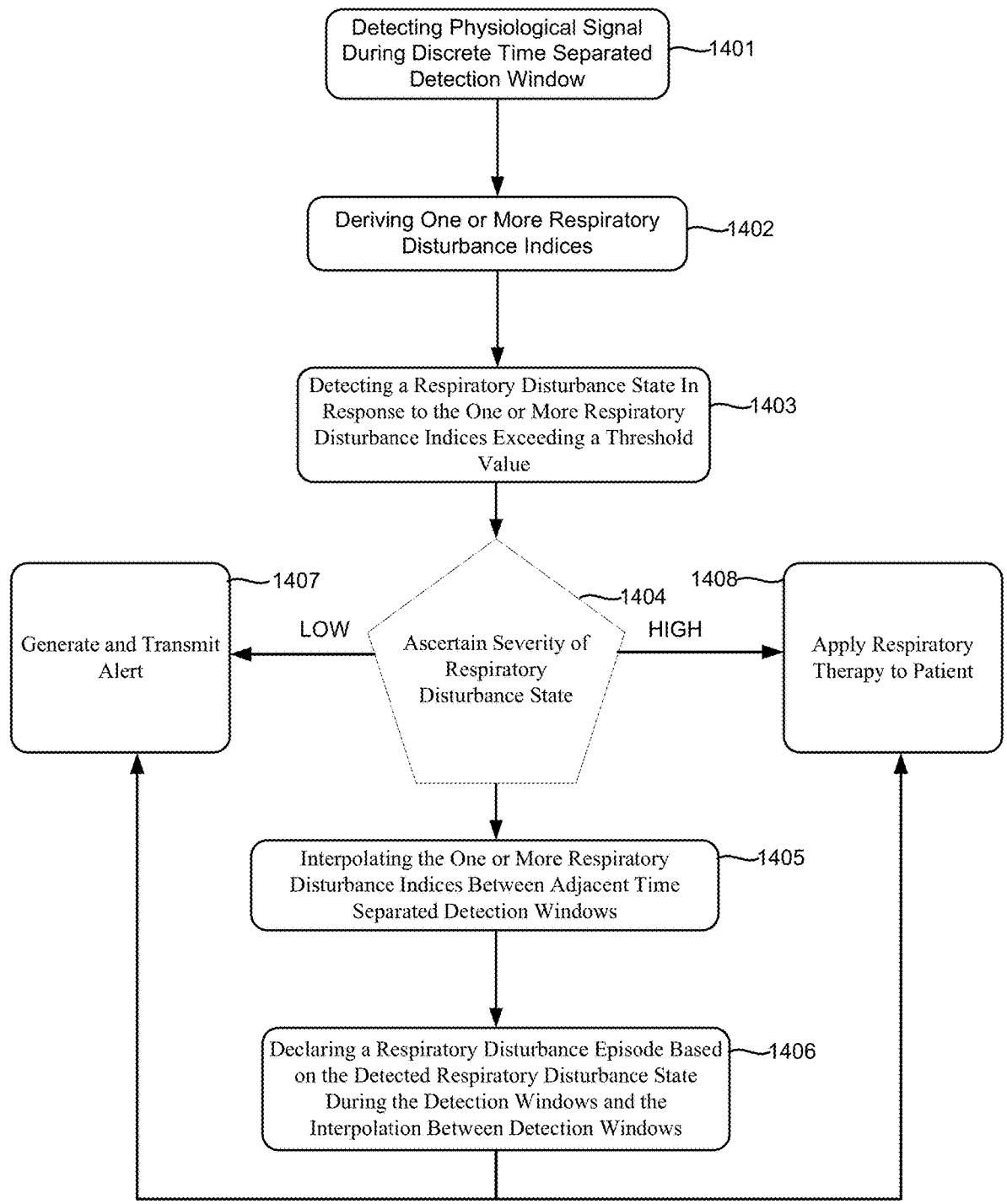
FIG. 14 is a flow diagram that includes an application of respiratory therapy to a patient according to one embodiment.

FIG. 14 shows a flow diagram that includes an application of respiratory therapy to a patient. According to the flow diagram, a physiological signal is captured 1401 in discrete time separated detection windows and one or more respiratory disturbance indices are derived 1402 from the physiological signal. Based upon the one or more respiratory disturbance indices deviating from a threshold value a respiratory disturbance state can be declared 1403. The severity of the respiratory disturbance state can be ascertained 1404. In some cases if the severity of the respiratory disturbance state is low, an alert can be generated and transmitted 1407.

As shown in FIG. 14, the method can interpolate 1405 one or more respiratory disturbance indices between adjacent time separated detection windows and can declare 1406 a respiratory disturbance episode based on the detected respiratory disturbance state during the detection windows and the interpolation between detection windows. In some cases, if the respiratory disturbance episode is declared, the alert can be generated and transmitted 1407. In other cases, if the severity of the respiratory disturbance state is high and/or the respiratory disturbance episode is declared/repeatedly declared (and/or e.g., alerts are repeatedly generated over a predetermined period of time, etc.), a respiratory therapy based upon the respiratory disturbance state can be applied to the patient 1408. Data can be tracked in real-time allowing for closed-loop therapy (e.g., CPAP, APAP (Automatic Positive Airway Pressure), ventilation, administration of gas or drugs such as oxygen or anesthesia) to be applied.

CONCLUSION

The above description is intended to be illustrative, and not restrictive. For example, the above-described examples (or one or more aspects thereof) may be used in combination with each other. Other examples may be used, such as by one of ordinary skill in the art upon reviewing the above description. Also, in the above Detailed Description, various features may be grouped together to streamline the disclosure. This should not be interpreted as intending that an unclaimed disclosed feature is essential. Rather, inventive subject matter may lie in less than all features of a particular disclosed example.

What is claimed is:

1. A method, comprising the steps of:
   a) providing a waveform acquisition apparatus configured to detect an electrocardiogram (ECG) signal during at least two discrete detection windows delineated from each other by an intermediate separation time, wherein the waveform acquisition apparatus is configured to not detect the ECG signal during the intermediate separation time;
   b) using the waveform acquisition apparatus to detect an ECG signal during at least two discrete detection windows delineated from each other by an intermediate separation time, each of the at least two discrete detection windows having a duration corresponding to at least a plurality of heartbeats;
   c) deriving one or more respiratory disturbance indices from the ECG signal in each of the at least two discrete detection windows;
   d) detecting a respiratory disturbance state in response to the one or more respiratory disturbance indices deviating from a threshold value in each of the at least two discrete detection windows delineated by the intermediate separation time;
   e) interpolating the one or more respiratory disturbance indices between an ending state and a subsequent beginning state of the at least two discrete detection windows delineated by the intermediate separation time; and
   f) determining whether a respiratory disturbance episode has occurred based on:
      i) the detected respiratory disturbance states during the at least two discrete detection windows; and
      ii) the interpolation between the at least two discrete detection windows,
      iii) wherein the respiratory disturbance episode is determined if the respiratory disturbance state is present in both the ending state and the subsequent beginning state of the at least two discrete detection windows and in the interpolation between the at least two discrete detection windows.

2. The method of claim 1, wherein the step of interpolating comprises interpolating one or more of heart activity and muscle activity between the ending state and the subsequent beginning state of the at least two discrete detection windows delineated by the intermediate separation time.

3. The method of claim 1, wherein the respiratory disturbance episode is not determined if the respiratory disturbance state is not present at both the ending state and the subsequent beginning state of the at least two discrete detection windows delineated by the intermediate separation time.

4. The method of claim 1, wherein the step of interpolating is based upon a priori information regarding a patient wellness.

5. The method of claim 1, wherein the step of interpolating is based upon learned information regarding a patient wellness.

6. The method of claim 1, wherein the step of interpolating is based upon one or more of a standard deviation, a variance, a personalized change, a normalized index, a physician set index, a percentage change of a preceding value, an absolute change, a relative change, and an adaptive threshold.

7. The method of claim 1, wherein the threshold value comprises one or more of a standard deviation, a variance, a personalized change, a normalized index, a physician set index, a percentage change of a preceding value, an absolute change, a relative change, and an adaptive threshold.

8. The method of claim 1, wherein the respiratory disturbance indices comprise one or more of a tidal volume intensity, a periodicity, and a turbulence.

9. The method of claim 1, wherein the threshold value is triggered based upon one or more of a threshold proportion of the at least two discrete detection windows delineated by the intermediate separation time, a trend in collected data, and an Apnea-Hypopnea Index (AHI) score.

10. The method of claim 1, further comprising the step of applying a respiratory therapy based upon detection of the respiratory disturbance episode.

11. The method of claim 1, further comprising the steps of providing for:
    a) a clinician set mode of operation; and
    b) a patient set sleep mode of operation,
    c) wherein the patient set sleep mode of operation one or both shortens the intermediate separation time between the at least two discrete detection windows for increased data capture, and, as compared to the clinician set mode of operation, increases a rate of data transmission during the at least two discrete detection windows delineated by the intermediate separation time.

12. The method of claim 1, wherein the ECG signal comprises a subcutaneously extrathoracic detected ECG signal.

13. The method of claim 1, further comprising the step of correlating the one or more respiratory disturbance indices with both heart activity and muscle activity.

14. The method of claim 1, further comprising the step of shortening the separation time between the at least two discrete detection windows in response to detection of the respiratory disturbance state.

15. The method of claim 1, further comprising the step of lengthening the separation time between the at least two discrete detection windows in response to detection of a normal breathing state.

16. A method, comprising the steps of:
    a) providing a waveform acquisition apparatus configured to detect an electrocardiogram (ECG) signal during at least two discrete detection windows delineated from each other by an intermediate separation time, wherein the waveform acquisition apparatus is configured to not detect the ECG signal during the intermediate separation time;

b) using the waveform acquisition apparatus to detect an ECG signal from a patient during at least two discrete detection windows delineated from each other by an intermediate separation time, each of the at least two discrete detection windows having a duration corresponding to at least a plurality of heartbeats;

c) deriving one or more respiratory disturbance indices from the ECG signal in each of the at least two detection windows delineated by the intermediate separation time;

d) detecting a respiratory disturbance state in response to the one or more respiratory disturbance indices deviating from a threshold value in each of the at least two detection windows delineated by the intermediate separation time;

e) interpolating the one or more respiratory disturbance indices between an ending state and a subsequent beginning state of the at least two discrete detection windows;

f) determining whether a respiratory disturbance episode has occurred based on:
  i) the detected respiratory disturbance states during the at least two discrete detection windows delineated by the intermediate separation time; and
  ii) the interpolation between the at least two discrete detection windows,
  iii) wherein the respiratory disturbance episode is determined if the respiratory disturbance state is present in both the ending state and the subsequent beginning state of the at least two discrete detection windows and in the interpolation between the at least two discrete detection windows;

g) determining a severity of the detected respiratory disturbance states; and h) generating one of a plurality of outputs in response to the severity of the detected respiratory disturbance states.

17. The method of claim 16, wherein:
a) determining the severity of the detected respiratory disturbance states comprises determining whether the severity of the detected respiratory disturbance states is low or high; and
b) generating one of the plurality of outputs comprises:
  i) generating and transmitting an alert in response to the low severity determination; and
  ii) applying a respiratory therapy to the patient in response to the high severity determination.

18. The method of claim 1, wherein the respiratory disturbance episode is not determined if the respiratory disturbance state is not present at both the ending state and the subsequent beginning state of the at least two discrete detection windows delineated by the intermediate separation time.

19. The method of claim 1, further comprising the steps of:
a) shortening the intermediate separation time between the at least two discrete detection windows in response to detection of the respiratory disturbance state; and
b) lengthening the intermediate separation time between the at least two discrete detection windows in response to detection of a normal breathing state.

20. The method of claim 1, further comprising the steps of providing for:
a) a clinician set mode of operation; and
b) a patient set sleep mode of operation,
c) wherein the patient set sleep mode of operation one or both shortens the intermediate separation time between the at least two discrete detection windows for increased data capture, and, as compared to the clinician set mode of operation, increases a rate of data transmission during the at least two discrete detection windows delineated by the intermediate separation time.

21. A method, comprising the steps of:
a) providing a waveform acquisition apparatus configured to detect an electrocardiogram (ECG) signal during a first detection window and a second detection window, the first and second detection windows being separated by a discrete time, wherein the waveform acquisition apparatus is configured to not detect the ECG signal during the discrete time separating the first and second detection windows;

b) using the waveform acquisition apparatus to detect an ECG signal during the first and second detection windows, each of the first and second detection windows having a duration corresponding to at least a plurality of heartbeats;

c) deriving one or more respiratory disturbance indices from the ECG signal in each of the first and second detection windows;

d) detecting a respiratory disturbance state in response to the one or more respiratory disturbance indices deviating from a threshold value in each of the first and second detection windows; and e) determining whether a respiratory disturbance episode has occurred based on the detected respiratory disturbance states during the first and second detection windows, wherein the respiratory disturbance episode is determined if the respiratory disturbance state is present in both the ending state of the first detection window and the beginning state of the second detection window.

22. The method of claim 21, further including the steps of:
a) interpolating the one or more respiratory disturbance indices between an ending state of the first detection window and a beginning state of the second detection window; and
b) determining whether the respiratory disturbance episode has occurred if the respiratory disturbance state is present in both the ending state of the first detection window and the beginning state of the second detection window and in the interpolation between the at least two discrete detection windows.

* * * * *